United States Patent
Thayumanavan et al.

(10) Patent No.: US 9,868,821 B2
(45) Date of Patent: Jan. 16, 2018

(54) POLYMERIC NANOGELS WITH DEGRADABLE BACKBONES AND FROM GRAS COMPONENTS, AND COMPOSITIONS AND METHODS THEREOF

(71) Applicant: University of Massachusetts, Boston, MA (US)

(72) Inventors: Sankaran Thayumanavan, Amherst, MA (US); Rajasekhar R. Ramireddy, Amherst, MA (US)

(73) Assignee: University of Massachusetts, Boston, MA (US)

(*) Notice: Subject to any disclaimer, the term of this patent is extended or adjusted under 35 U.S.C. 154(b) by 1 day.

(21) Appl. No.: 14/848,466

(22) Filed: Sep. 9, 2015

(65) Prior Publication Data
US 2016/0075829 A1    Mar. 17, 2016

Related U.S. Application Data

(60) Provisional application No. 62/047,878, filed on Sep. 9, 2014.

(51) Int. Cl.
| | | |
|---|---|---|
| C08G 69/48 | (2006.01) | |
| C08J 3/11 | (2006.01) | |
| A61K 47/48 | (2006.01) | |
| A61K 9/51 | (2006.01) | |
| C08G 69/10 | (2006.01) | |
| C08G 69/26 | (2006.01) | |

(52) U.S. Cl.
CPC ............ *C08G 69/48* (2013.01); *A61K 9/5146* (2013.01); *C08G 69/10* (2013.01); *C08G 69/26* (2013.01)

(58) Field of Classification Search
None
See application file for complete search history.

(56) References Cited

FOREIGN PATENT DOCUMENTS

WO    WO -2012162307    * 11/2012

* cited by examiner

*Primary Examiner* — Jianfeng Song
(74) *Attorney, Agent, or Firm* — Milstein Zhang & Wu LLC

(57) ABSTRACT

The invention generally relates to novel polymers and polymeric nanogels having biodegradable polymeric backbones, and compositions and methods of preparation and use thereof, for example, as guest-host polymer nano-assemblies and nano-delivery vehicles, which offer utilities in diverse fields including drug delivery, diagnostics and specialty materials.

4 Claims, 18 Drawing Sheets

*Scheme 1*

*Scheme 1*

Aspartic and Glutamic acid containing self-crosslinked polymer nanogel

R=H: Poly(-L-Serine ester)-graft-PEG, PDS
R=CH₃: Poly(-L-Threonine ester)-graft-PEG, PDS Serine and threonine containing
self-crosslinked polyester nanogel

POLYMERIC NANOGELS WITH DEGRADABLE BACKBONES AND FROM GRAS COMPONENTS, AND COMPOSITIONS AND METHODS THEREOF

PRIORITY CLAIMS AND RELATED APPLICATIONS

This application claims the benefit of U.S. Provisional Application No. 62/047,878, filed Sep. 9, 2014, the entire content of which is incorporated herein by reference in its entirety.

GOVERNMENT RIGHTS

The United States Government has certain rights to the invention pursuant to Grant No. GM-065255 awarded by the National Institutes of Health and to Grant No. W911NF-13-1-0187 awarded by the U. S. Army Research Office.

TECHNICAL FIELDS OF THE INVENTION

The invention generally relates to polymers and polymer-based nano-structures. More particularly, the invention relates to novel polymers and polymeric nanogels having biodegradable polymeric backbones, and compositions and methods of preparation and use thereof, for example, as guest-host polymer nano-assemblies and nano-delivery vehicles, which offer utilities in diverse fields including drug delivery, diagnostics and specialty materials.

BACKGROUND OF THE INVENTION

Recently, nanoparticles have played an increasingly significant role in diverse fields such as microelectronics, multiphase catalysis, sensing and therapeutics. (*Nanoparticles: From Theory to Application*; Schmid, Ed.; Wiley-VCH: Essen, 2004; Zhang, et al. *Self-Assembled Nanostructures*; Nanostructure Science and Technology Series; Springer: 2002; *Nanoparticles: Building Blocks for Nanotechnology*; Rotello, Ed.; Springer: 2003; Daniel, et al. 2004 *Chem. Rev.* 104, 293.) The ability to encapsulate and release guest molecules within the nanoparticle interior is required for applications such as sensing and therapeutics. For many applications, facile modulation of the nanoparticle surface is also important in order to obtain appropriate interfacial properties.

Amphiphilic molecules readily self-assemble into nano-assemblies, such as micelles and liposomes, which can encapsulate guest molecules within their interior spaces. (Harada, et al. 2006 *Progress in Poly. Sci.* 31, 949-982; O'Reilly, et al. 2006 *Chem. Soc. Rev.* 35, 1068-1083; Zhu, et al. 2012 *J. Mat. Chem.* 22, 7667-7671; Owen, et al. 2012 *Nano Today* 7, 53-65; Sawant, et al. 2010 *Soft Matter* 6, 4026-4044; Micheli, et al. 2012 *Recent Patents on CNS Drug Discovery* 7, 71-86.)

A major challenge remains in developing polymeric nanogels wherein the backbones are fully degradable. In particular, methodologies are highly desired that allow significant control over the degradation of polymer backbones to small molecules that are generally regarded as safe (GRAS). This challenge is magnified due to the need to maintain a hydrophilic-lipophilic balance that is necessary for retention of the fidelity of the assembly while allowing efficient surface functionalization.

With regard to the development of drug delivery systems, significant attention has been paid to cancer therapy because of the severity and often-fatal nature of the disease. (Siegel, et al. 2014 *CA-Cancer J. Clin.* 64, 9-29.) Nanocarriers have emerged as a superior class of drug delivery system as they can exploit the leaky vasculature of tumor tissues for selective uptake. (Danhier, et al. 2010 *J. Controlled Release.* 148, 135-146; Maeda, et al. 2000 *J. Controlled Release.* 65, 271-284; Matsumura, et al. 1986 *Cancer Res.* 46, 6387-6392; Davis, et al. 2008 *Nat. Rev. Drug Discov.* 7, 771-782; Baban, et al. 1998 *Adv. Drug Deliv. Rev.* 34, 109-119; Duncan 2003 *Nat. Rev. Drug Discov.* 2, 347-360; Gillies, et al. 2005 *Drug Discovery Today* 10, 35-43; Peer, et al. 2007 *Nat. Nanotechnol.* 2, 751-760; Haag 2004 *Angew. Chem. Int. Ed.* 43, 278-282; Allen, et al. 2004 *Scienc.* 303, 1818-1822.)

Amongst the nanocarriers that are being developed for this purpose, polymeric micelles have attracted particular attention as these nanoassemblies can noncovalently encapsulate the hydrophobic drug molecules in aqueous conditions. (Kale, et al. 2009 *Langmuir* 25, 9660-9670; Koo, et al. 2005 *Nanomedicine: NBM* 1, 193-212; Liu, et al. 2009 *Macromolecules* 42, 3-13; Kataoka, et al. 2001 *Adv. Drug Delivery Rev.* 47, 113-131; Savic, et al. 2003 *Science* 300, 615-618; Torchilin 2001 *J. Controlled Release* 73, 137-172; Yin, et al. 2008 *J. Controlled Release* 131, 2-4; Kwon, et al. 1995 *Adv. Drug Delivery Rev.* 16, 295-309; Li, et al. 2014 *Chem. Commun.* 50, 13417-13432; Jeong, et al. 1997 *Nature* 388, 860-862; Kwon, et al. 1996 *Adv. Drug Delivery Rev.* 21, 107-116; Gref, et al. 1994 *Science* 263, 1600-1603.) Although polymer micelles show great promise in many cases, these assemblies face a general conundrum with respect to drug loading and encapsulation stability.

For high encapsulation stability, it is necessary that the hydrophobic part of the micellar assembly is glassy so as to keep the guest molecules from leaking into the bulk. On the other hand, if the interior of the assembly is glassy, loading the drug molecules become an issue. The successful utility of polymer micelles in the drug delivery area has demonstrated that 'sweet spots' can indeed be identified to develop useful nanocarriers. A complementary approach that can offer a viable solution to this issue involves chemically crosslinked polymeric assemblies, where the loading can occur when the assemblies are rather lose and the encapsulation stability is achieved due to the crosslinking-induced incarceration of the drug molecules. (Ryu, et al. 2010 *J. Am. Chem. Soc.* 132, 8246-8247; Oh, et al. 2008 *Prog. Polym. Sci.* 33, 448-477; Molla, et al. 2014 *Biomacromolecules* 15, 4046-4053; Rossler, et al. 2012 *Adv. Drug Delivery Rev.* 64, 270-279; Peppas, et al. 2000 *Eur. J. Pharm. Biopharm.* 50, 27-46.) Such a crosslinking strategy also offers the opportunity to program the assemblies to uncrosslink and release its contents only in the presence of a specific stimulus. (Ganta, et al. 2008 *J. Controlled Release* 126, 187-204; Shenoy, et al. 2005 *Pharm. Res.* 22, 2107-2114; Shenoy, et al. 2005 *Mol. Pharmacol.* 2, 357-366; Kommareddy, et al. 2005 *Bioconjug. Chem.* 16, 1423-1432; Meyer, et al. 2001 *J. Control. Release.* 74, 213-224; Saito, et al. 2003 *Adv. Drug Deliv.* 55, 199-215; Arrueboa, et al. 2007 *Nano Today* 2, 22-32; Ito, et al. 2005 *J. Biosci. Bioeng.* 100, 1-11; Rapoport, et al. 2002 *Drug Deliv. Syst. Sci.* 2, 37-46; Gao, et al. 2005 *J. Control. Release* 102, 203-221; Rapoport 2007 *Prog. Polym. Sci.* 32, 962-990.)

As safety of the drug carriers is of utmost importance, it is critical that a carrier is biocompatible. (Matsumura, et al. 2009 *Cancer Sci.* 100, 572-579; Kim, et al. 2004 *Clin. Cancer Res.* 10, 3708; Matsumura, et al. 2004 *Br. J. Cancer.* 91, 1775-1781; Hamaguchi, et al. 2010 *Clin. Cancer Res.* 16, 5058-5066; Katti, et al. 2002 *Adv. Drug Delivery Rev.* 54, 933-961; Ulery, et al. 2011 *J. Polym. Sci., Part B: Polym.*

*Phys.* 49, 832-864; Friess Eur. 1998 *J. Pharm. Biopharm.* 45, 113-136; Middleton, et al. 2000 *Biomaterials* 21, 2335-2346; Deng, et al. 2012 *Nano Today* 7, 467-480.)

Thus, there is a continued need for novel approach to develop biocompatible scaffolds is to design the components of the assembly such that they are biodegradable and that the degradation products are non-toxic.

SUMMARY OF THE INVENTION

The invention provides novel polymers and polymeric nanogels having biodegradable polymeric backbones, and compositions and methods of preparation and use thereof, for example, as guest-host polymer nano-assemblies and nano-delivery vehicles, which offer utilities in diverse fields including drug delivery, diagnostics and specialty materials.

The invention provides stimuli responsive polymeric nanogels, wherein the polymer is designed such that the degraded products are composed of molecules that are generally accepted to be biocompatible, more particularly, molecules that are GRAS (generally regarded as safe). (http://www.fda.gov/Food/IngredientsPackagingLabeling/GRAS/)

Drug delivery systems based on biocompatible molecules that not only encapsulate a hydrophobic drug molecule, but also release it in response to a specific trigger are of utmost importance for therapeutic and biomedical applications.

In one aspect, the biodegradable polymers of the invention include a polymeric backbone selected from backbones of polyamides, polyesters and polycarbonates.

In another aspect, the biodegradable polymeric nanogel of the invention is designed to release encapsulated guests (e.g., drug or diagnostic payloads) in response to defined biologically, physically or chemically relevant stimuli (e.g., glutathione concentration inside the cells, a change in pH, redox reagent, redox potential, ionic strength, enzymatic activity, protein concentration, light, heat, or mechanical stress).

In yet another aspect, the nano-assembly of the invention includes a host crosslinked polymer network having a biodegradable polymeric backbone, and is typically surface functionalized with one or more functional groups to allow modifiable surface functionalities (e.g., to introduce targeting capabilities); and one or more guest molecular cargos (e.g., non-covalently encapsulated in the host crosslinked polymer network). The host crosslinked polymer network is addressable by a biological, physical or chemical intervention (e.g., glutathione concentration inside the cells, a change in pH, redox reagent, redox potential, ionic strength, enzymatic activity, protein concentration, light, heat, or mechanical stress) resulting in partial or complete degradation and/or descrosslinking of the host polymer network and release of the guest molecular cargo from the nano-assembly.

In yet another aspect, the biodegradable polymers and nano-assemblies of the invention are biodegradable into molecules that are generally regarded as safe (GRAS).

DEFINITIONS

Figure 1:
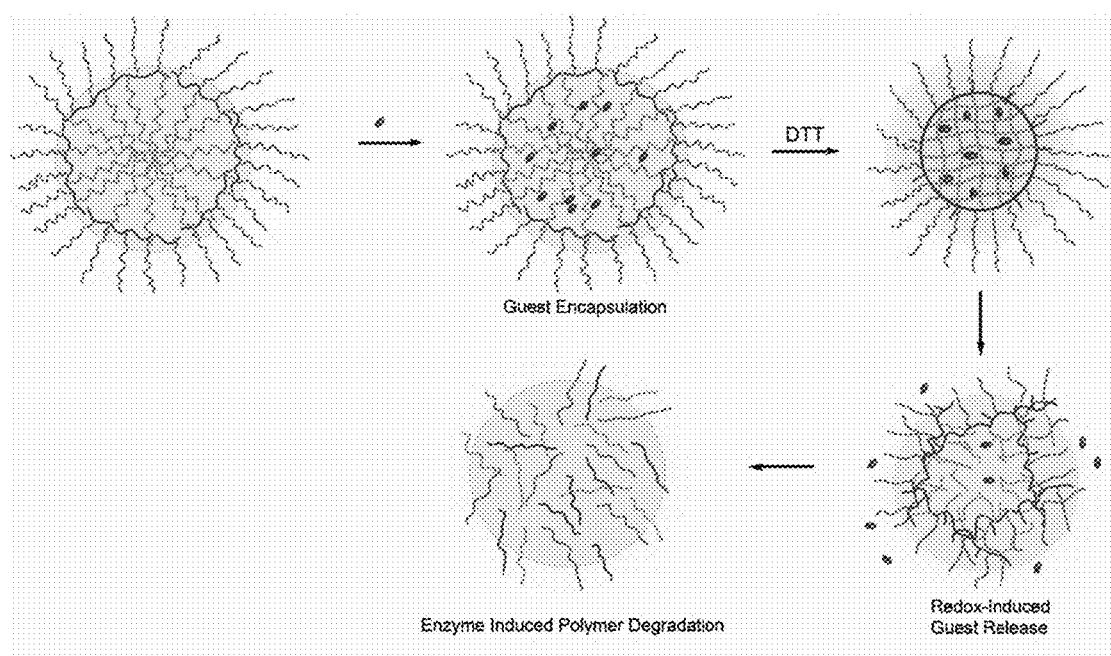
FIG. 1. Scheme 1. A schematic illustration of an exemplary embodiment of the biodegradable polymer nanogel delivery system.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 2006. It will be appreciated that the compounds, as described herein, may be substituted with any number of substituents or functional moieties.

As used herein, "$C_x$-$C_y$" refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{15}$", "$C_1$-$C_{20}$" and the likes similarly encompass the various combinations between 1 and 20 (inclusive) carbon atoms, such as $C_1$-$C_6$, $C_1$-$C_{12}$, $C_3$-$C_{12}$ and $C_6$-$C_{12}$.

As used herein, the term "alkyl", refers to a hydrocarbyl group, which is a saturated hydrocarbon radical having the number of carbon atoms designated and includes straight, branched chain, cyclic and polycyclic groups. The term "hydrocarbyl" refers to any moiety comprising only hydrogen and carbon atoms. Hydrocarbyl groups include saturated (e.g., alkyl groups), unsaturated groups (e.g., alkenes and alkynes), aromatic groups (e.g., phenyl and naphthyl) and mixtures thereof.

As used herein, the term "$C_x$-$C_y$" alkyl refers to a saturated linear or branched free radical consisting essentially of x to y carbon atoms, wherein x is an integer from 1 to about 10 and y is an integer from about 2 to about 20. Exemplary $C_x$-$C_y$ alkyl groups include "$C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc.

As used herein, the term "halogen" refers to fluorine (F), chlorine (Cl), bromine (Br), or iodine (I).

As used herein, the term "biological, physical or chemical interventions" includes a change in pH, redox reagent, redox potential, ionic strength, enzymatic activity, protein concentration, light (e.g., UVA, UVB or UVC), heat, or mechanical stress.

DESCRIPTION OF THE INVENTION

The invention provides novel polymers and polymeric nanogels having biodegradable polymeric backbones, and compositions and methods of preparation and use thereof, for example, as guest-host polymer nano-assemblies and nano-delivery vehicles, which offer utilities in diverse fields including drug delivery, diagnostics and specialty materials.

The polymers, polymeric nanogels and nano-assemblies and nano-delivery vehicles of the invention can be prepared via simple and reliable synthetic techniques.

The polymeric nanogels disclosed herein not only exhibit responsive molecular release, but also show high in vitro cellular viability on HEK 293T, MCF7, A549 and HeLa cell lines. The toxicity of these nanogels was further evaluated using mouse preimplantation embryo development as a highly sensitive toxicity assay, where blastocysts were formed after 4 days of in vitro culture and live pups were born when morulae/early blastocysts were transferred to the uteri of recipients. These results indicate that these nanogels are non-toxic during early mammalian development and do not alter normal growth.

In one aspect, the invention generally relates to a crosslinked biodegradable polymer having a polymeric backbone biodegradable into small molecules in response to a relevant biological, physical or chemical stimuli.

In certain preferred embodiments, the polymeric backbone is selected from polyamides, polyesters and polycarbonates.

In certain preferred embodiments, wherein the biodegradable polymer comprises one or more hydrophilic functional groups and one or more crosslinkable hydrophobic group as part of its side chain.

In another aspect, the invention generally relates to a biodegradable polymeric nanogel comprising the crosslinked biodegradable polymer disclosed herein.

In certain preferred embodiments, the biodegradable polymeric nanogel has encapsulated therein one or more drug or diagnostic payloads, releaseable in response to defined biologically, physically or chemically relevant stimuli. In certain preferred embodiments, wherein the biologically, physically or chemically relevant stimuli is selected from glutathione concentration inside the cells, a change in pH, redox reagent, redox potential, ionic strength, enzymatic activity, protein concentration, light, heat, and mechanical stress.

In yet another aspect, the invention generally relates to a nano-assembly, the nano-assembly includes: a host crosslinked polymer network having a biodegradable polymeric backbone, and is surface functionalized with one or more functional groups; and one or more guest molecular cargos non-covalently encapsulated in the host crosslinked polymer network. The host crosslinked polymer network is addressable by a biological, physical or chemical stimuli resulting in partial or complete degradation and/or descrosslinking of the host polymer network and release of the guest molecular cargo from the nano-assembly.

In certain preferred embodiments, the one or more functional groups are adapted to incorporate one or more of small molecule ligands, peptides, proteins, antibodies and aptamers.

In certain preferred embodiments, the biologically, physically or chemically relevant stimuli is selected from glutathione concentration inside the cells, a change in pH, redox reagent, redox potential, ionic strength, enzymatic activity, protein concentration, light, heat, and mechanical stress.

In certain preferred embodiments, the biodegradable polymer comprises a polyamide backbone. In certain preferred embodiments, the biodegradable polymer comprises a polyester backbone. In certain preferred embodiments, the biodegradable polymer comprises a polycarbonate backbone.

In yet another aspect, the invention generally relates to a method for controlled delivery of an agent to a target biological site. The method includes: providing a nano-assembly of a host crosslinked polymer network non-covalently encapsulating therein a guest molecular cargo, wherein the host crosslinked polymer network is comprised of biodegradable polymeric backbones and is adapted to partial or complete decrosslinking and/or degraded by a biological, physical or chemical intervention resulting in release of the guest molecular cargo from the nano-assembly; delivering the nano-assembly to the target biological site; and causing a biological, physical or chemical intervention resulting in a partial or complete decrosslinking resulting in release of the guest molecular cargo from the nano-assembly.

In certain preferred embodiments, the guest molecular cargo is a therapeutic agent. In certain preferred embodiments, the guest molecular cargo is a diagnostic agent. In certain preferred embodiments, the guest molecular cargo is an imaging agent. In certain preferred embodiments, the guest molecular cargo is a small molecule. In certain preferred embodiments, the guest molecular cargo is a polypeptide. In certain preferred embodiments, the guest molecular cargo is an oligonucleotide. In certain preferred embodiments, the guest molecular cargo is an antitumor agent.

In certain preferred embodiments, the target biological site comprises a site inside a cell. In certain preferred embodiments, the target biological site comprises a site inside a tumor cell. In certain preferred embodiments, the target biological site comprises a specific tissue. In certain preferred embodiments, the target biological site comprises a tumor tissue.

In certain preferred embodiments of the crosslinked biodegradable polymer is characterized by a polymeric backbone that comprises:

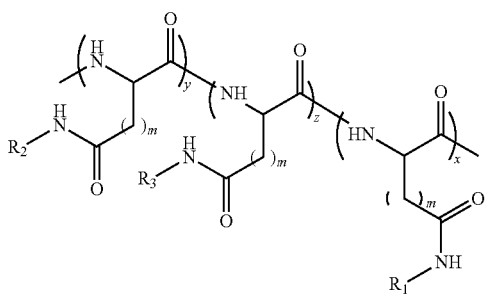

wherein
each m is independently an integer from about 1 to about 6 (e.g., 1, 2, 3, 4, 5, 6),
each of x and y is independently a positive number, z may be zero or a positive number,
$R_1$ is a charge-neutral hydrophilic group,
$R_2$ is a group comprising a crosslinking moiety, and
$R_3$ is a non-crosslinking group, selected from a linear or branched $C_1$-$C_{16}$ alkyl group.

In certain preferred embodiments of the crosslinked biodegradable polymer is characterized by a polymeric backbone that comprises:

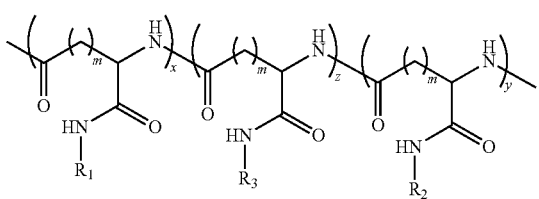

wherein
each m is independently an integer from about 1 to about 6 (e.g., 1, 2, 3, 4, 5, 6),
each of x and y is independently a positive number, z may be zero or a positive number,
$R_1$ is a charge-neutral hydrophilic group,
$R_2$ is a group comprising a crosslinking moiety, and
$R_3$ is a non-crosslinking group, selected from a linear or branched $C_1$-$C_{16}$ alkyl group.

In certain preferred embodiments of the crosslinked biodegradable polymer is characterized by a polymeric backbone that comprises:

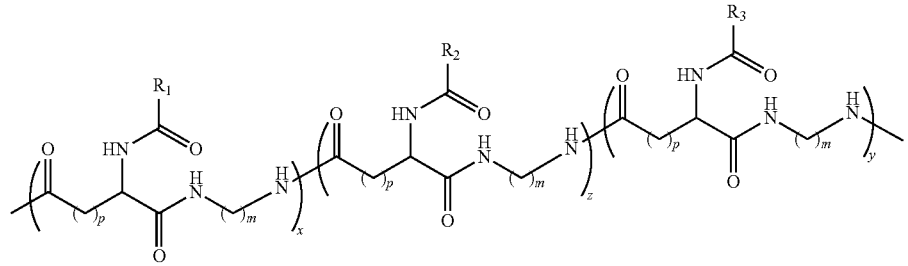

wherein
each m is independently an integer from about 1 to about 6 (e.g., 1, 2, 3, 4, 5, 6),
each m is independently an integer from about 1 to about 6 (e.g., 1, 2, 3, 4, 5, 6),
each of x and y is independently a positive number, z may be zero or a positive number,
$R_1$ is a charge-neutral hydrophilic group,
$R_2$ is a group comprising a crosslinking moiety, and
$R_3$ is a non-crosslinking group, selected from a linear or branched $C_1$-$C_{16}$ alkyl group.

In certain preferred embodiments of the crosslinked biodegradable polymer is characterized by a polymeric backbone that comprises:

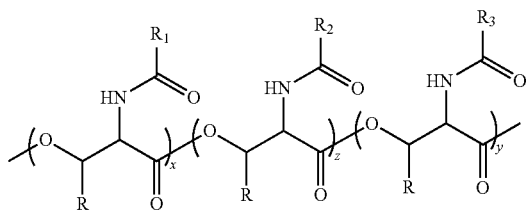

wherein
each of x and y is independently a positive number, z may be zero or a positive number,
$R_1$ is a charge-neutral hydrophilic group,
$R_2$ is a group comprising a crosslinking moiety,
$R_3$ is a non-crosslinking group, selected from a linear or branched $C_1$-$C_{16}$ alkyl group, and
R is hydrogen or a $C_1$-$C_{20}$ alkyl group.

In certain preferred embodiments of the crosslinked biodegradable polymer is characterized by a polymeric backbone that comprises:

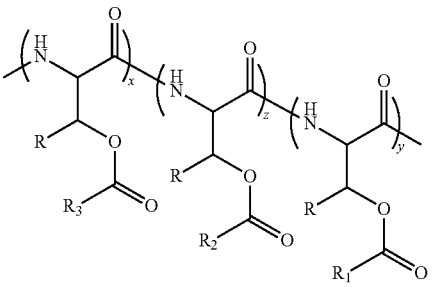

wherein
each of x and y is independently a positive number, z may be zero or a positive number,
$R_1$ is a charge-neutral hydrophilic group,
$R_2$ is a group comprising a crosslinking moiety, and
$R_3$ is a non-crosslinking group, selected from a linear or branched $C_1$-$C_{16}$ alkyl group.

In certain preferred embodiments of the crosslinked biodegradable polymer is characterized by a polymeric backbone that comprises:

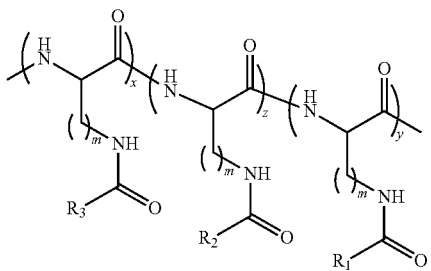

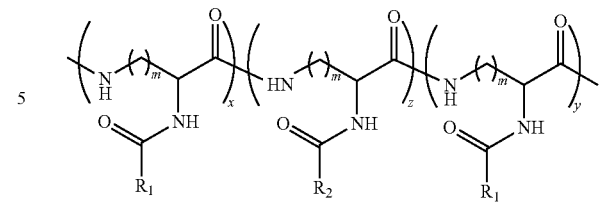

wherein
each m is independently an integer from about 1 to about 6 (e.g., 1, 2, 3, 4, 5, 6),
each of x and y is independently a positive number, z may be zero or a positive number,
$R_1$ is a charge-neutral hydrophilic group,
$R_2$ is a group comprising a crosslinking moiety, and
$R_3$ is a non-crosslinking group, selected from a linear or branched $C_1$-$C_{16}$ alkyl group.

In certain preferred embodiments of the crosslinked biodegradable polymer is characterized by a polymeric backbone that comprises:

wherein
each m is independently an integer from about 1 to about 6 (e.g., 1, 2, 3, 4, 5, 6),
each of x and y is independently a positive number, z may be zero or a positive number,
$R_1$ is a charge-neutral hydrophilic group,
$R_2$ is a group comprising a crosslinking moiety, and
$R_3$ is a non-crosslinking group, selected from a linear or branched $C_1$-$C_{16}$ alkyl group.

In certain preferred embodiments of the crosslinked biodegradable polymer is characterized by a polymeric backbone that comprises:

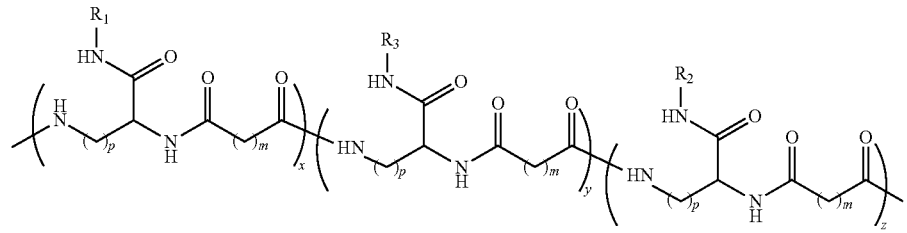

wherein
each m is independently an integer from about 1 to about 6 (e.g., 1, 2, 3, 4, 5, 6),
each of x and y is independently a positive number, z may be zero or a positive number,
$R_1$ is a charge-neutral hydrophilic group,
$R_2$ is a group comprising a crosslinking moiety, and
$R_3$ is a non-crosslinking group, selected from a linear or branched $C_1$-$C_{16}$ alkyl group.

In certain preferred embodiments of the crosslinked biodegradable polymer is characterized by a polymeric backbone that comprises:

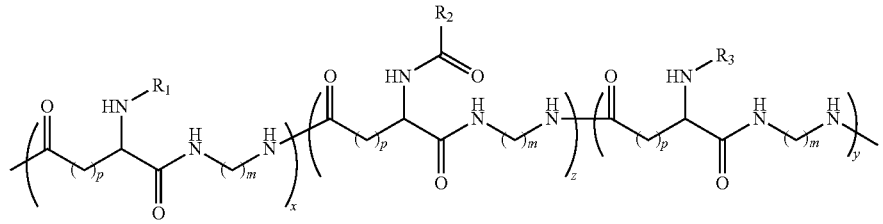

wherein
each m is independently an integer from about 1 to about 6 (e.g., 1, 2, 3, 4, 5, 6), each m is independently an integer from about 1 to about 6 (e.g., 1, 2, 3, 4, 5, 6), each of x and y is independently a positive number, z may be zero or a positive number, $R_1$ is a charge-neutral hydrophilic group, $R_2$ is a group comprising a crosslinking moiety, and $R_3$ is a non-crosslinking group, selected from a linear or branched $C_1$-$C_{16}$ alkyl group.

In certain preferred embodiments of the above-described polymeric backbones, $R_1$ is selected from

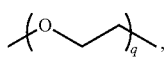

wherein q is an integer from 3 to about 100 (e.g., from 3 to about 50, from 3 to about 20, from 3 to about 10, from 3 to about 6, from 10 to about 100, from 20 to about 100), a zwitterionic group selected from:

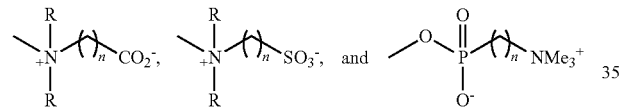

wherein each R is hydrogen or a $C_1$-$C_{20}$ alkyl group; n is independently an integer from about 1 to about 6 (e.g., 1, 2, 3, 4, 5, 6), or a charged functional group selected from —$CO_2^-$, —$HPO_3^-$, —$SO_3^-$, —$NR_2^-$, —$NR_3^+$, wherein each R is independently a hydrogen or a $C_1$-$C_{20}$ alkyl group.

In certain preferred embodiments of the above-described polymeric backbones, $R_2$ comprises at least one stimulus-sensitive functional group selected from disulfides, acetals, ketals, imines, hydrazides, and oximes.

In yet another aspect, the invention generally relates to a crosslinked biodegradable polymer that is biodegradable into molecules that are generally regarded as safe (GRAS).

In yet another aspect, the invention generally relates to a nano-assembly that is biodegradable into molecules that are generally regarded as safe (GRAS).

In yet another aspect, the invention generally relates to a method for controlled delivery of an agent to a target biological site, wherein the host crosslinked polymer network is biodegradable into molecules that are generally regarded as safe (GRAS).

In certain embodiments, the one or more functional groups are adapted to incorporate one or more of small molecule ligands, peptides, proteins, antibodies and aptamers.

In certain preferred embodiments, the biodegradable polymer of the invention includes a polyester or a polyamide backbone. An exemplary system having a PEGylated polyamide backbone having pendent disulfide groups is shown below.

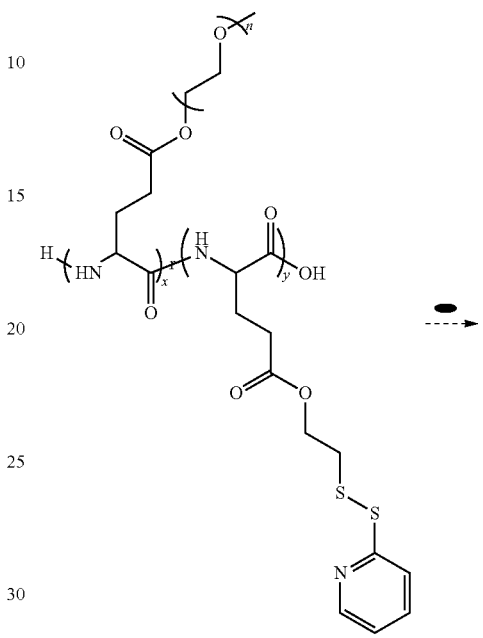

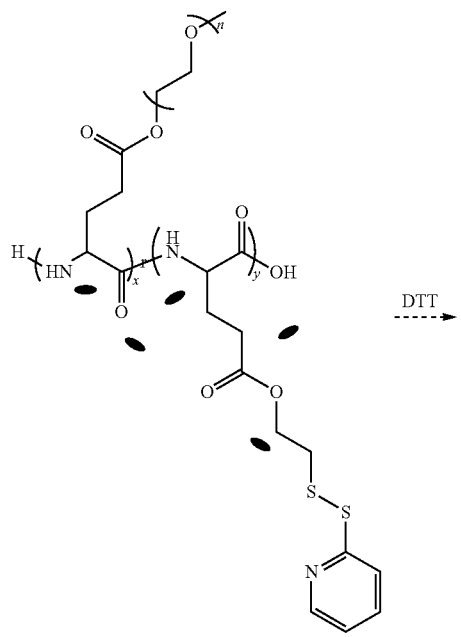

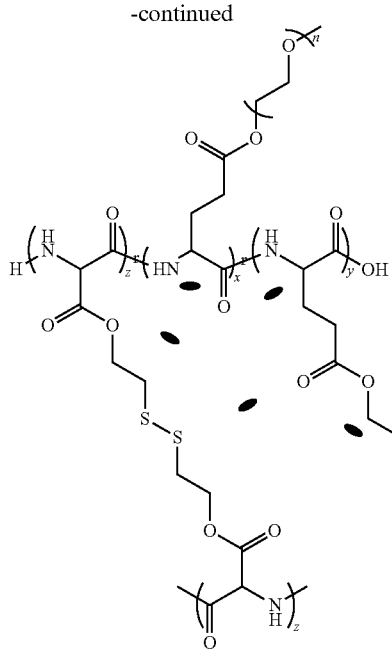

An exemplary synthetic scheme is provided below. It is understood that variations to the synthetic methodologies are available to a person skilled in the art in selecting the suitable approach in preparation of the desired polymers.

In certain preferred embodiments, the biodegradable polymer of the invention includes a polyester backbone. An exemplary system having a polyester backbone is shown below.

Figure 2:
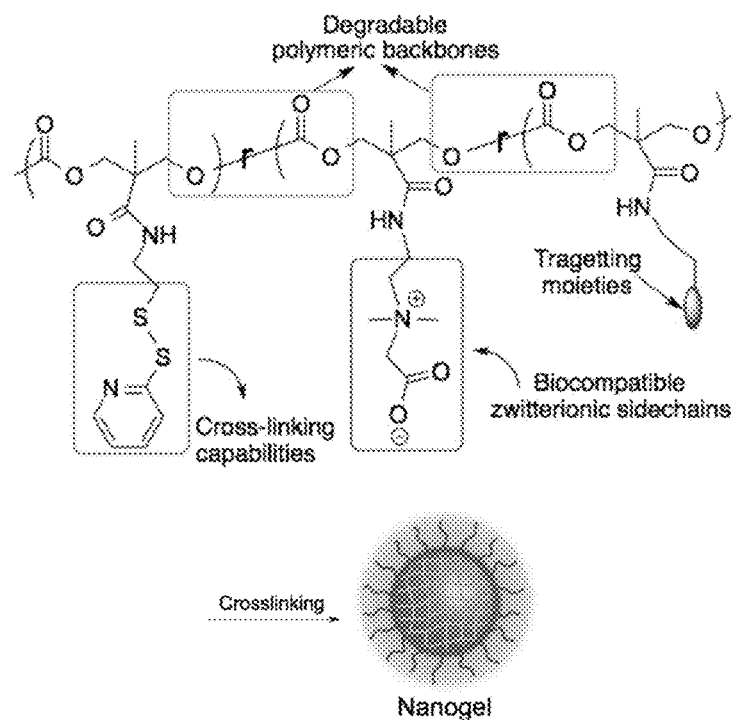
FIG. 2. Exemplary embodiment of a biodegradable polycarbonate backbone.

In certain preferred embodiments, the biodegradable polymer of the invention includes a polycarbonate backbone. An exemplary system having a polycarbonate backbone is shown in FIG. 2.

Figure 3:
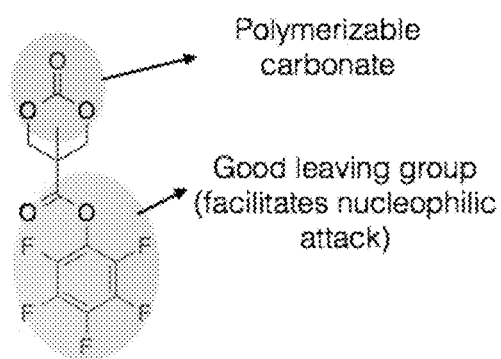
FIG. 3. Exemplary embodiment of monomers that may be used to form biodegradable polycarbonates.
Figure 4:
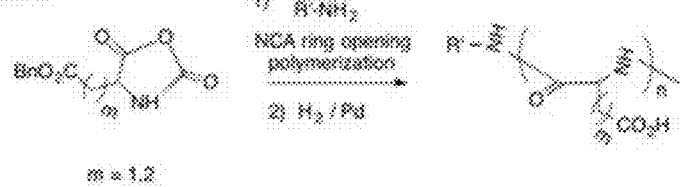
FIG. 4. Exemplary embodiments of aspartic and glutamic acid-containing self-crosslinked polymer nanogels.
Figure 4:
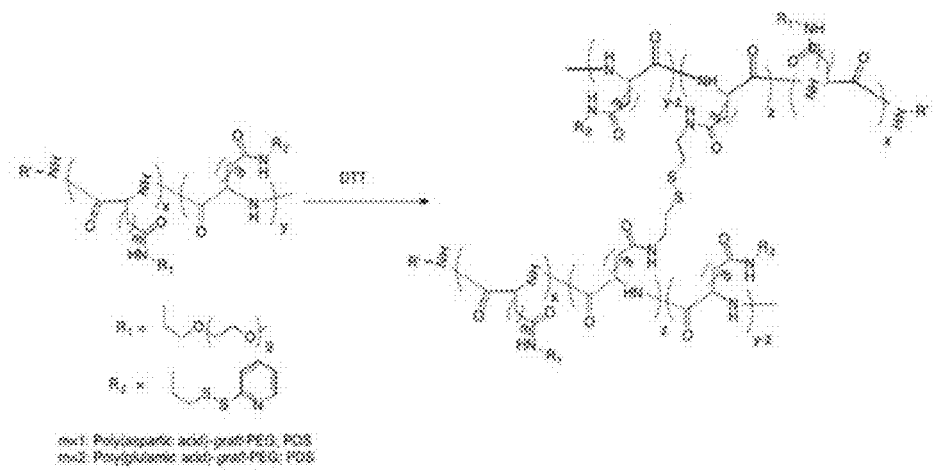
Figure 4:
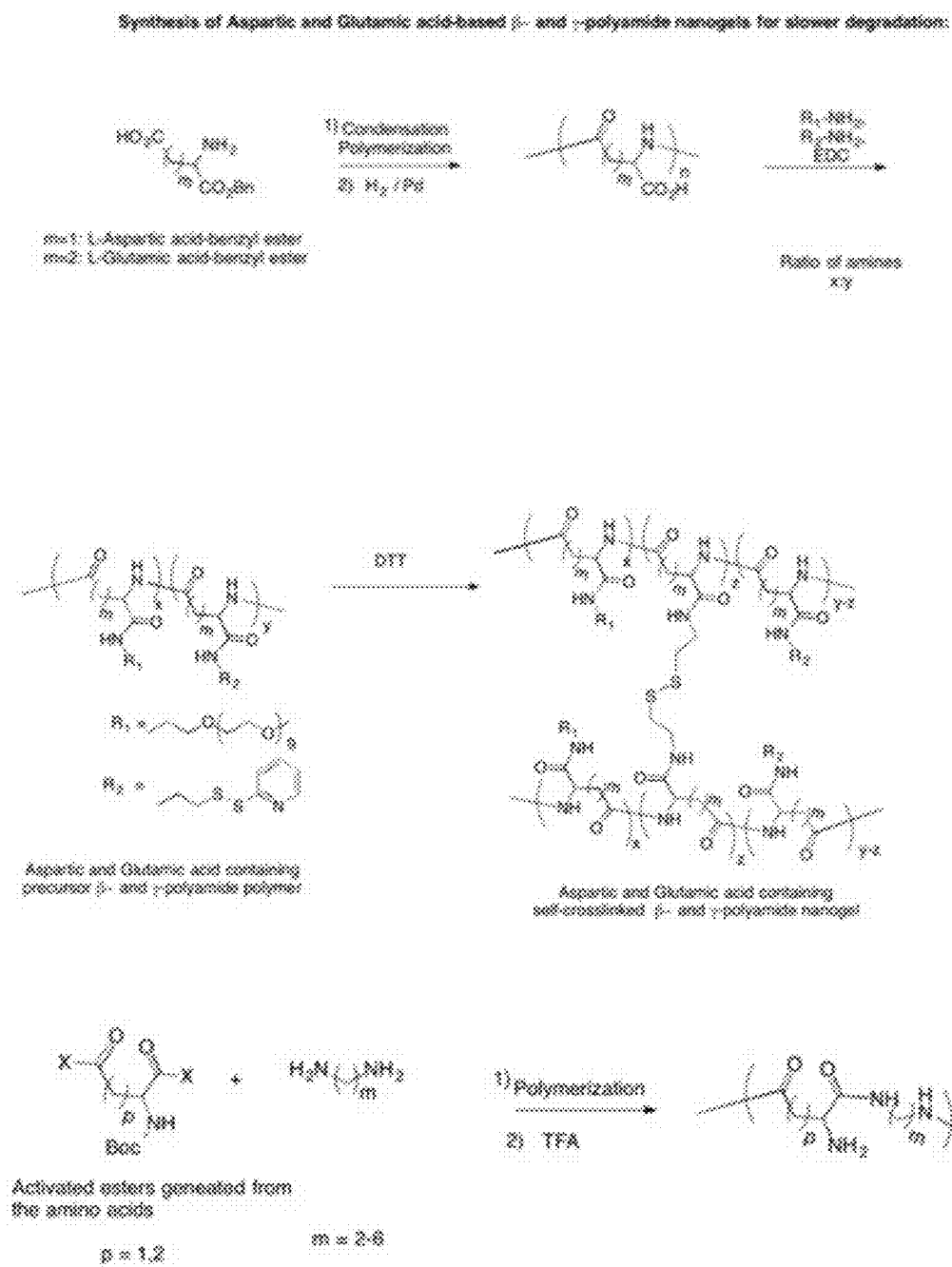
Figure 4:
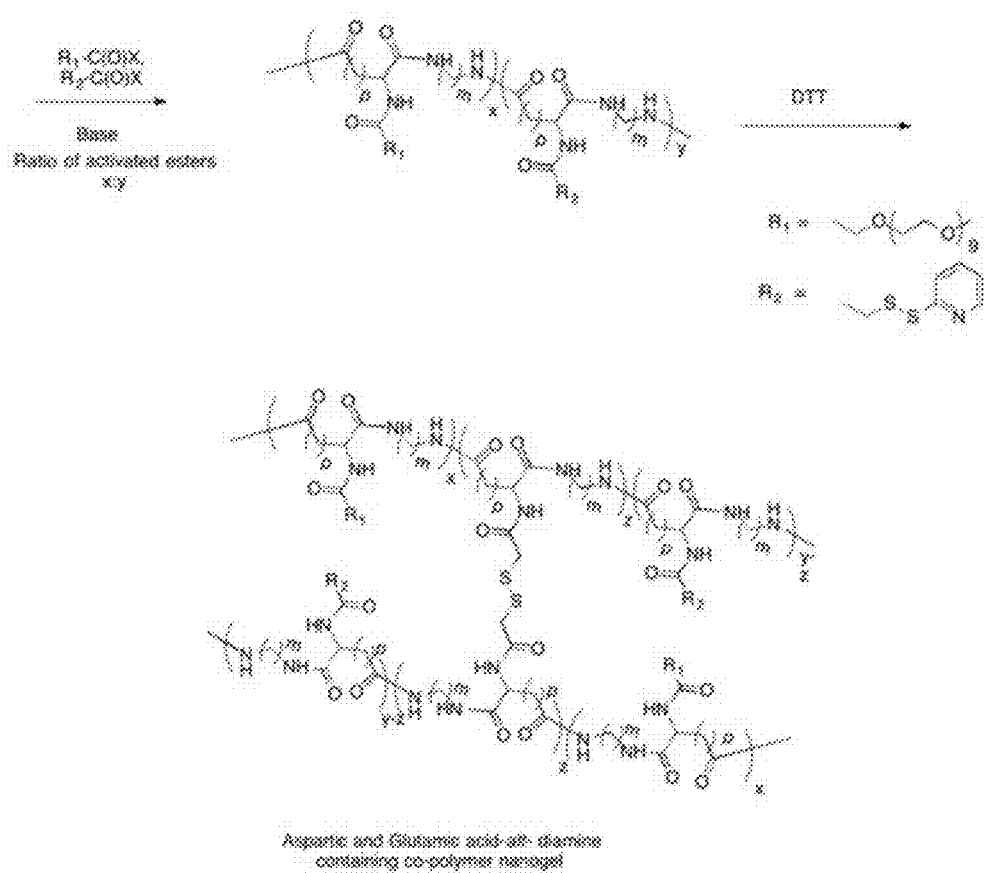
Figure 5:
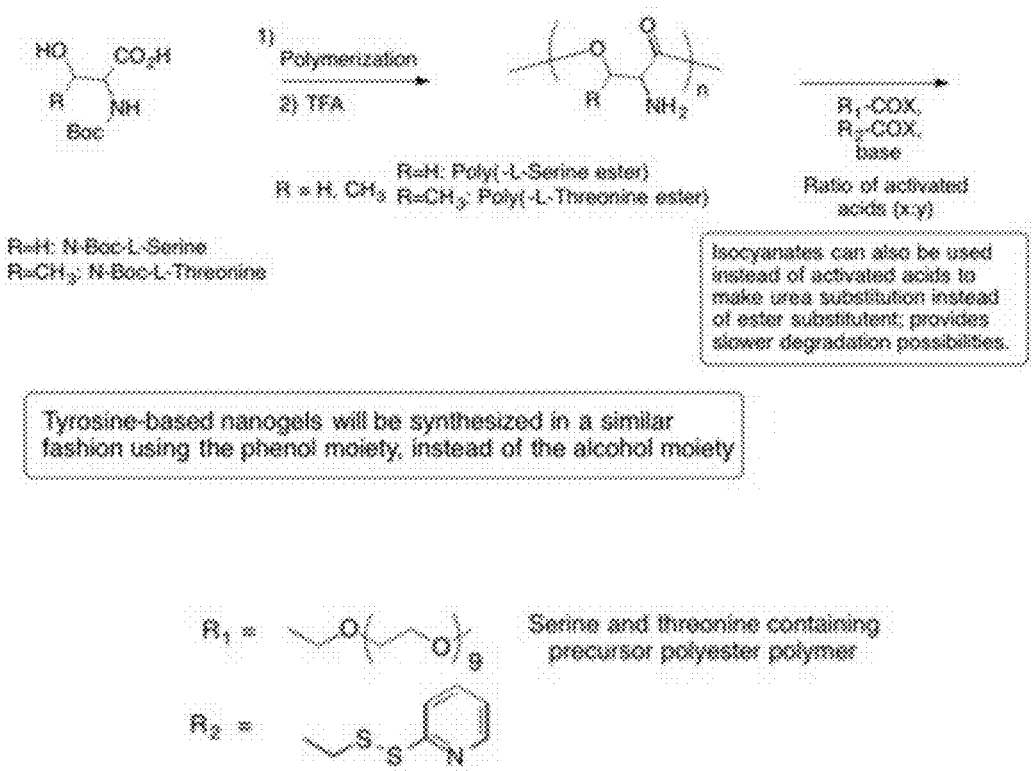
FIG. 5. Exemplary embodiments of serine and threonine-containing self-crosslinked polyester nanogels.
Figure 5:
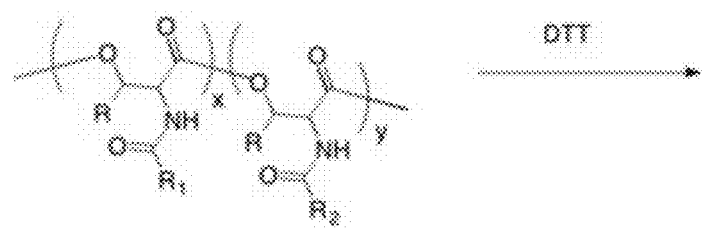
Figure 5:
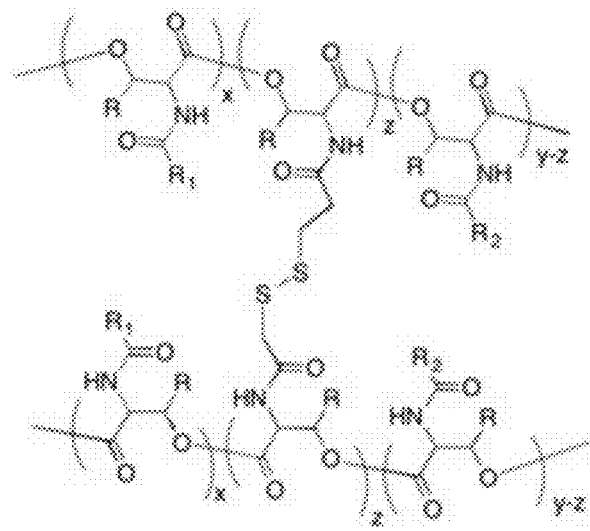
Figure 6:
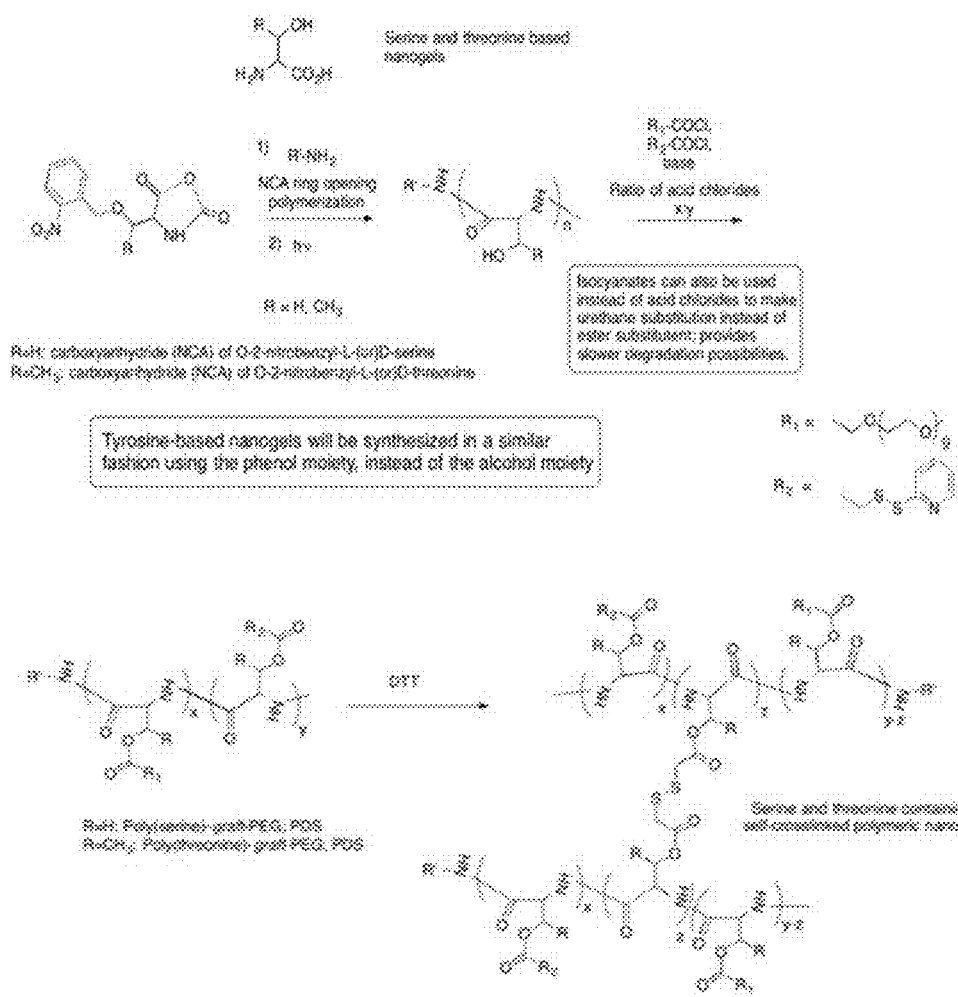
FIG. 6. Exemplary embodiments of serine and threonine-containing self-crosslinked polyester nanogels.
Figure 7:
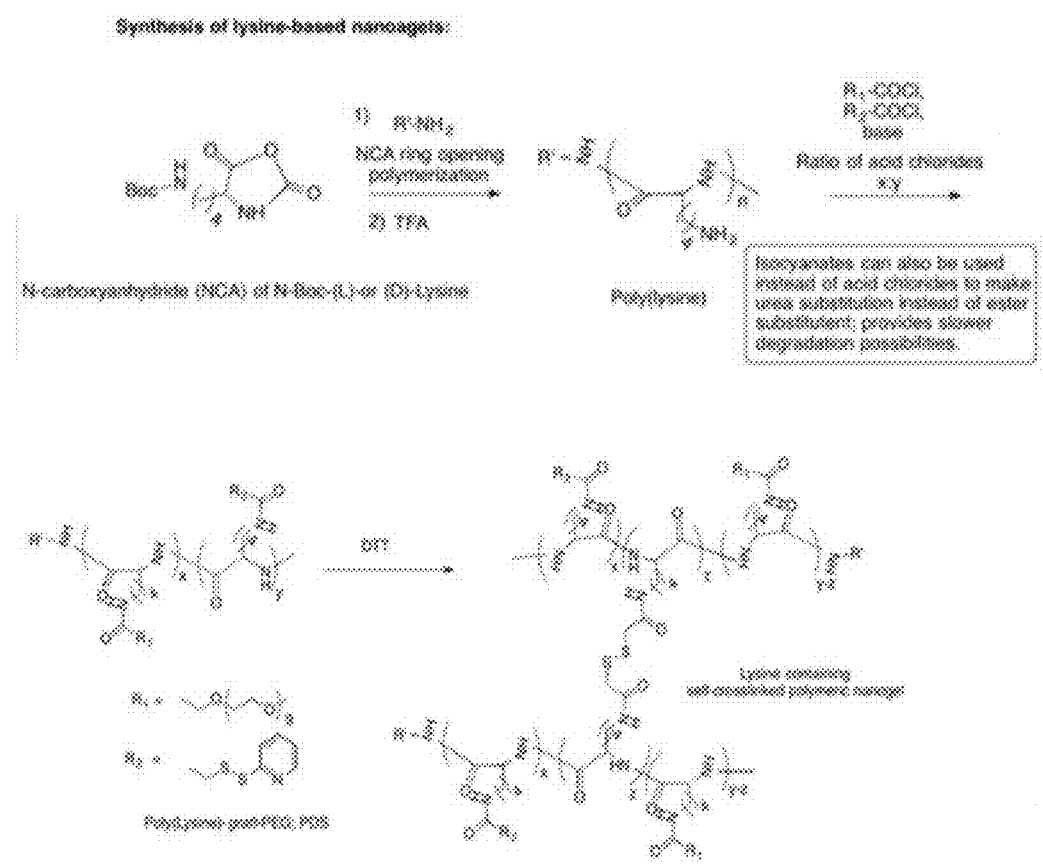
FIG. 7. Exemplary embodiments of lysine-containing self-crosslinked polymeric nanogels, serine and threonine-containing self-crosslinked polyamide, and lysine-containing copolymer nanogels.
Figure 7:
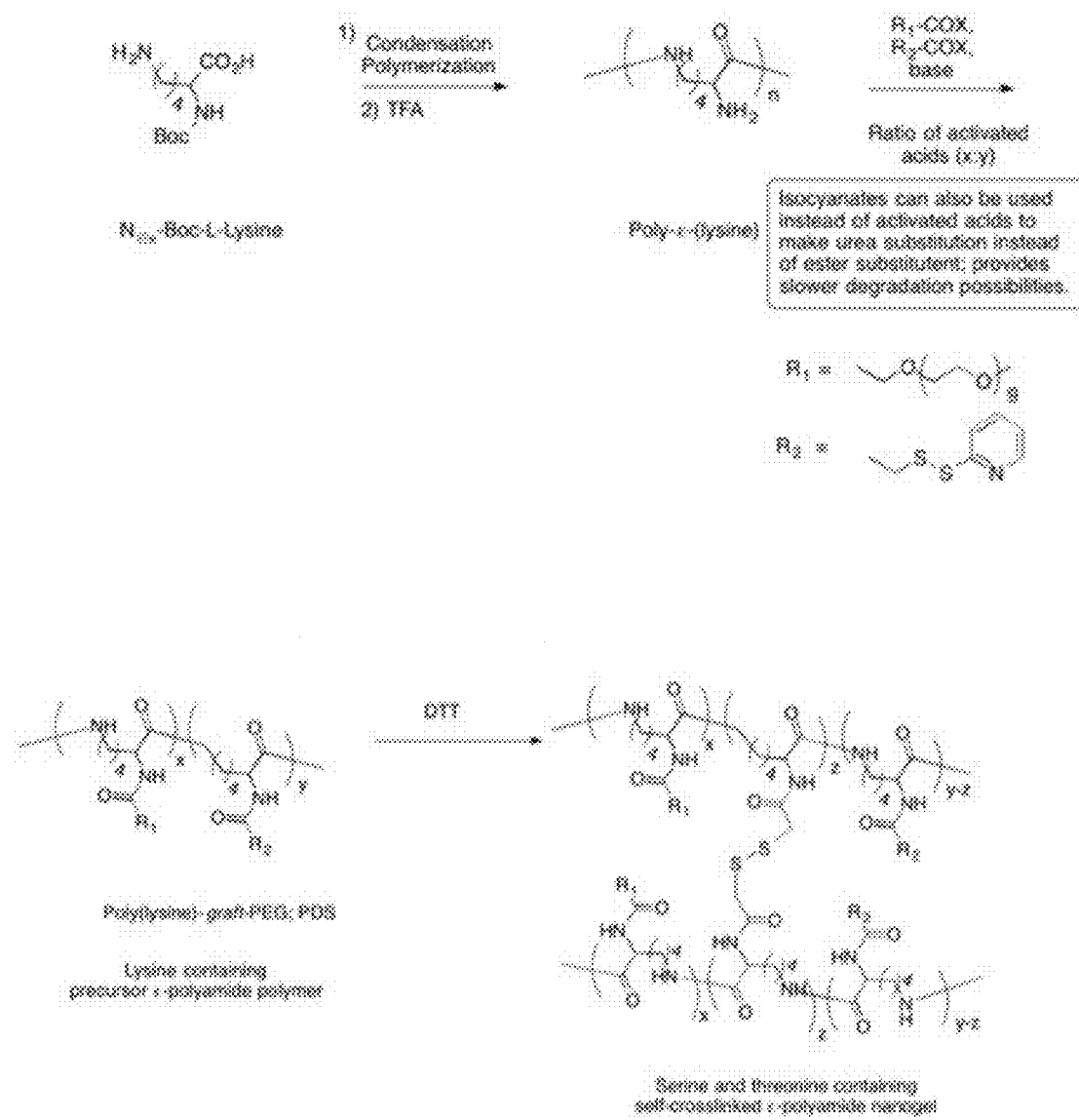
Figure 7:
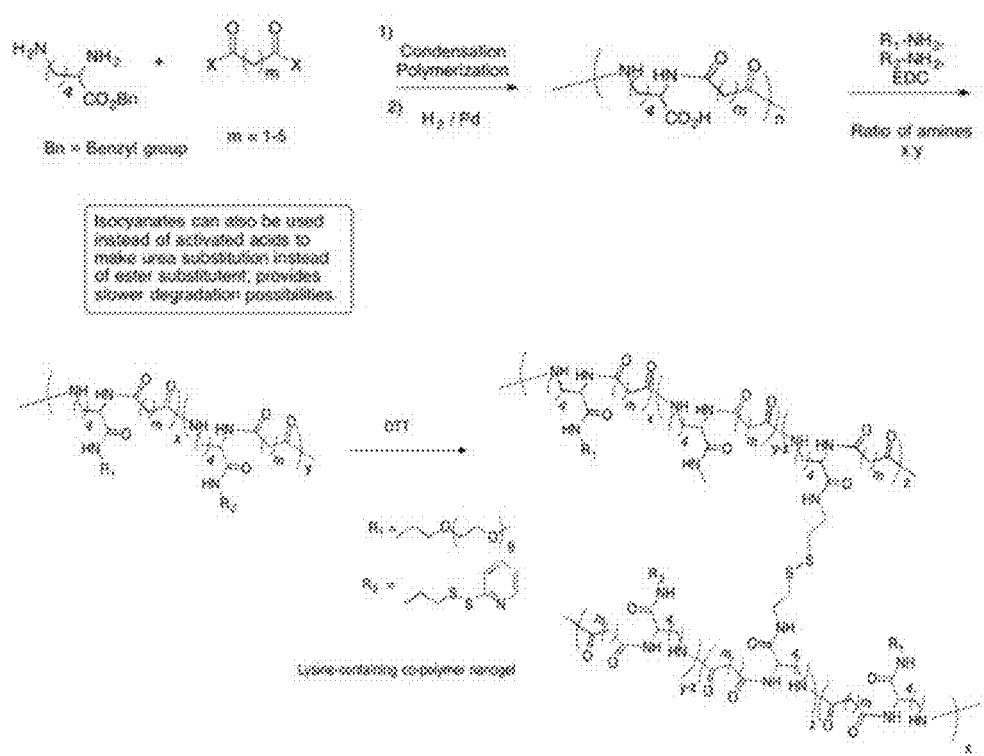

Exemplary monomers that may be used to form polycarbonates of the invention include those shown in FIG. 3, which may be synthesized according the following scheme, for example,

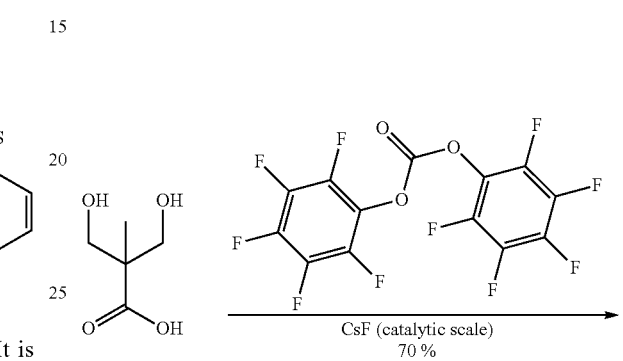

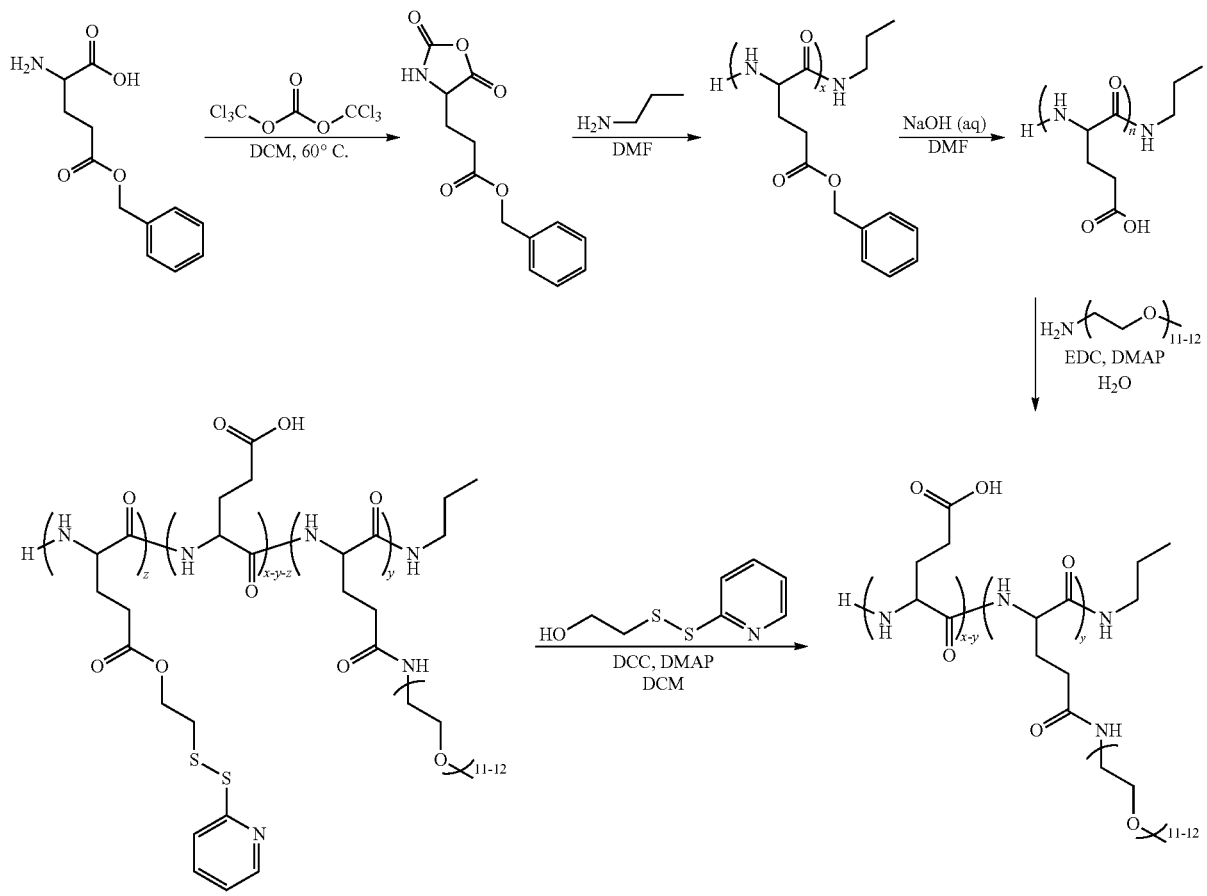

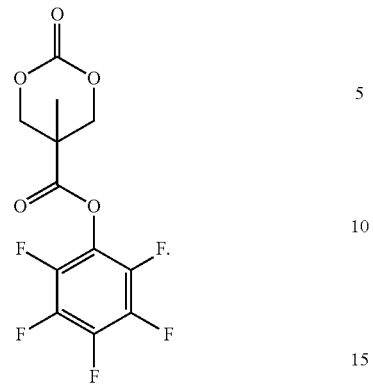
Hedrick et al. *J. Am. Chem Soc.*, 2010, 132 (42), pp 14724-14726
Functional cyclic carbonates include, for example, and polymerization of functional cyclic monomers provide functional polymers.
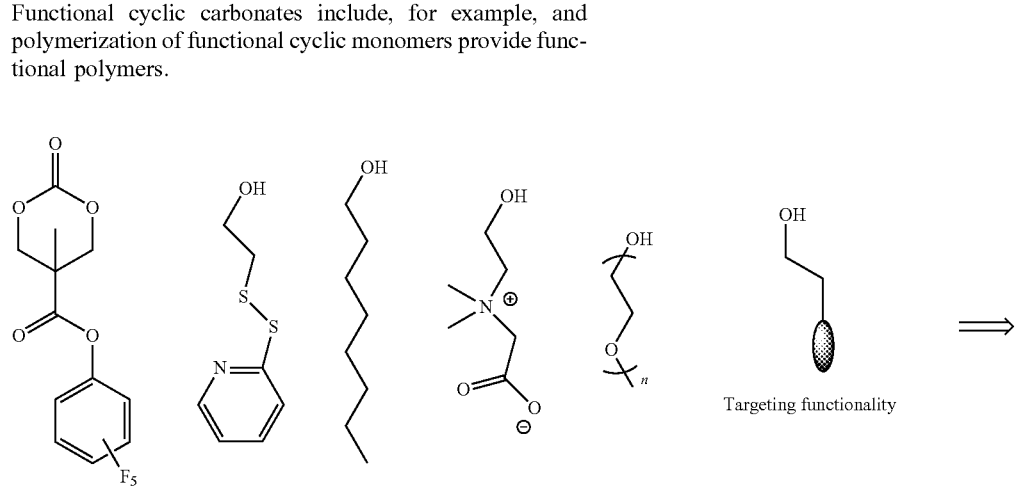
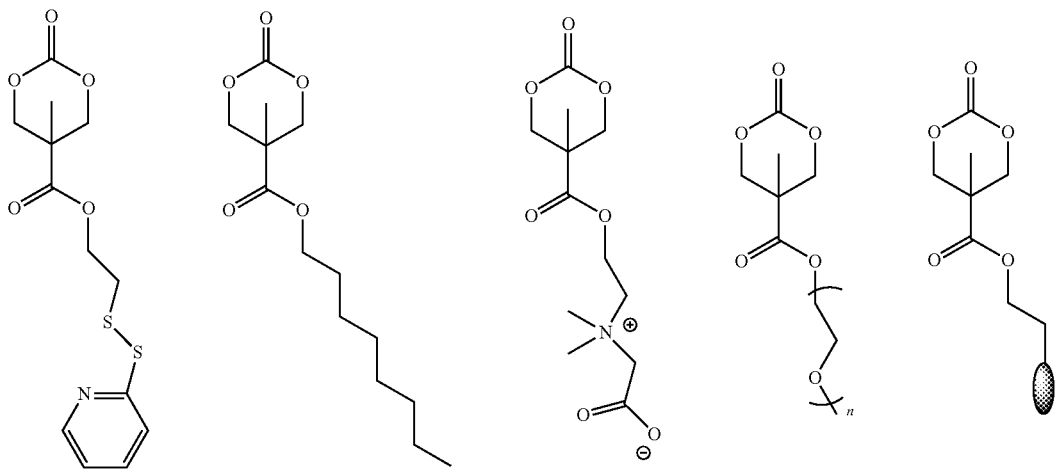

-continued
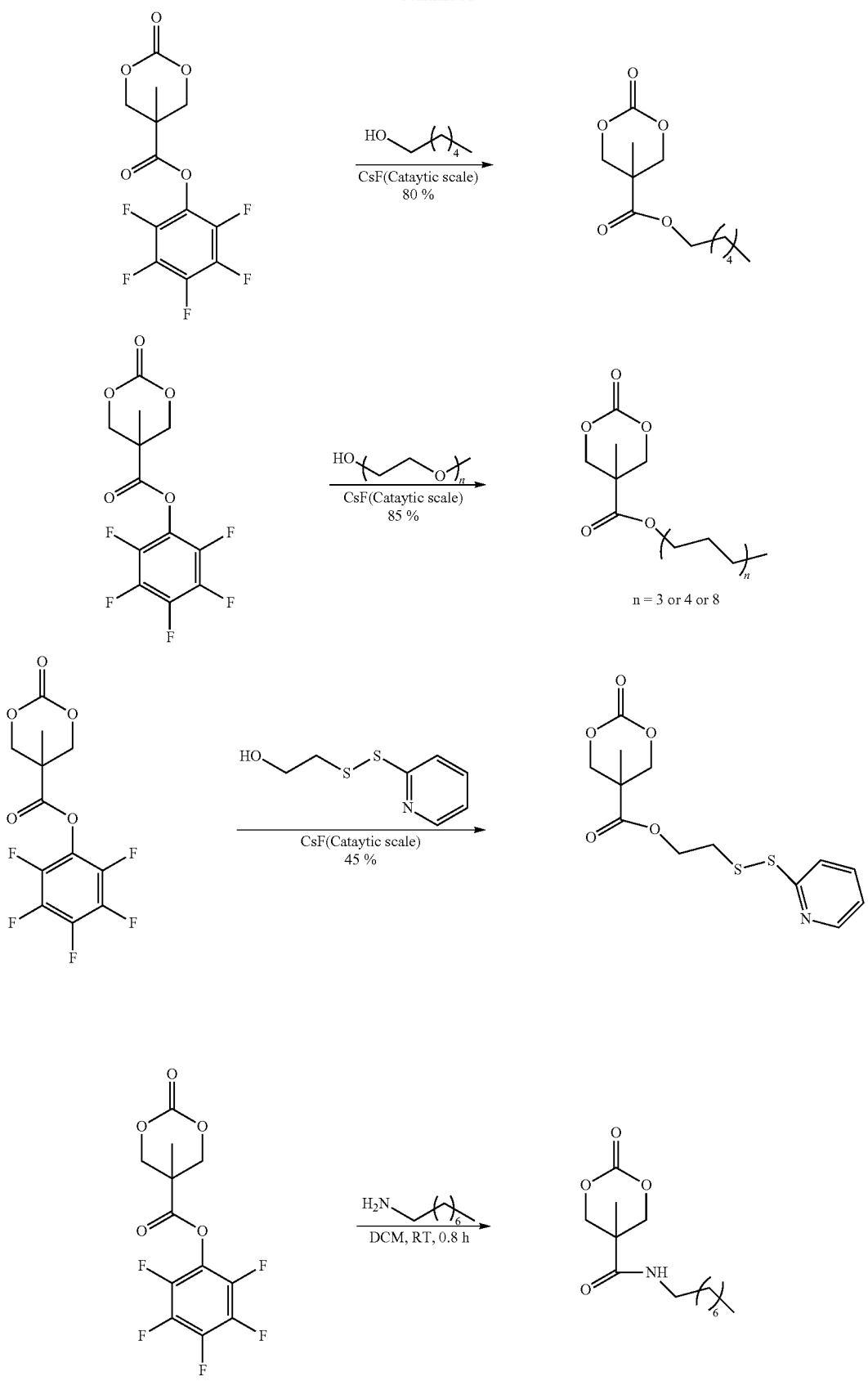
Amines:

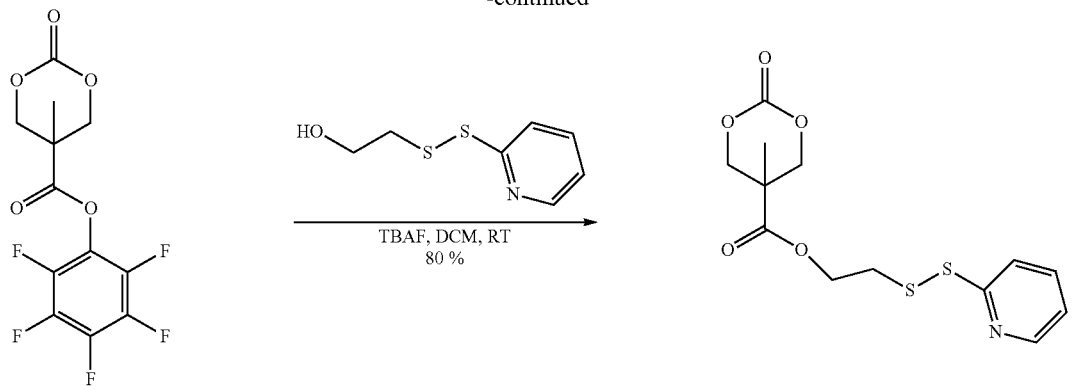
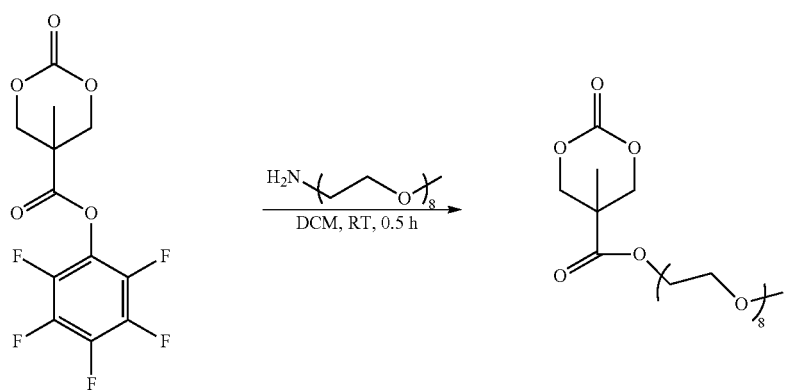
Exemplary methods for making random copolymers are shown below, including organocatalytic methods from monomers and post functionalization of reactive polycarbonates.
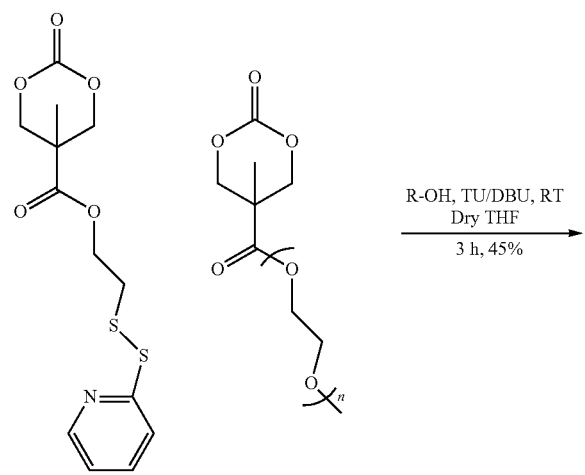

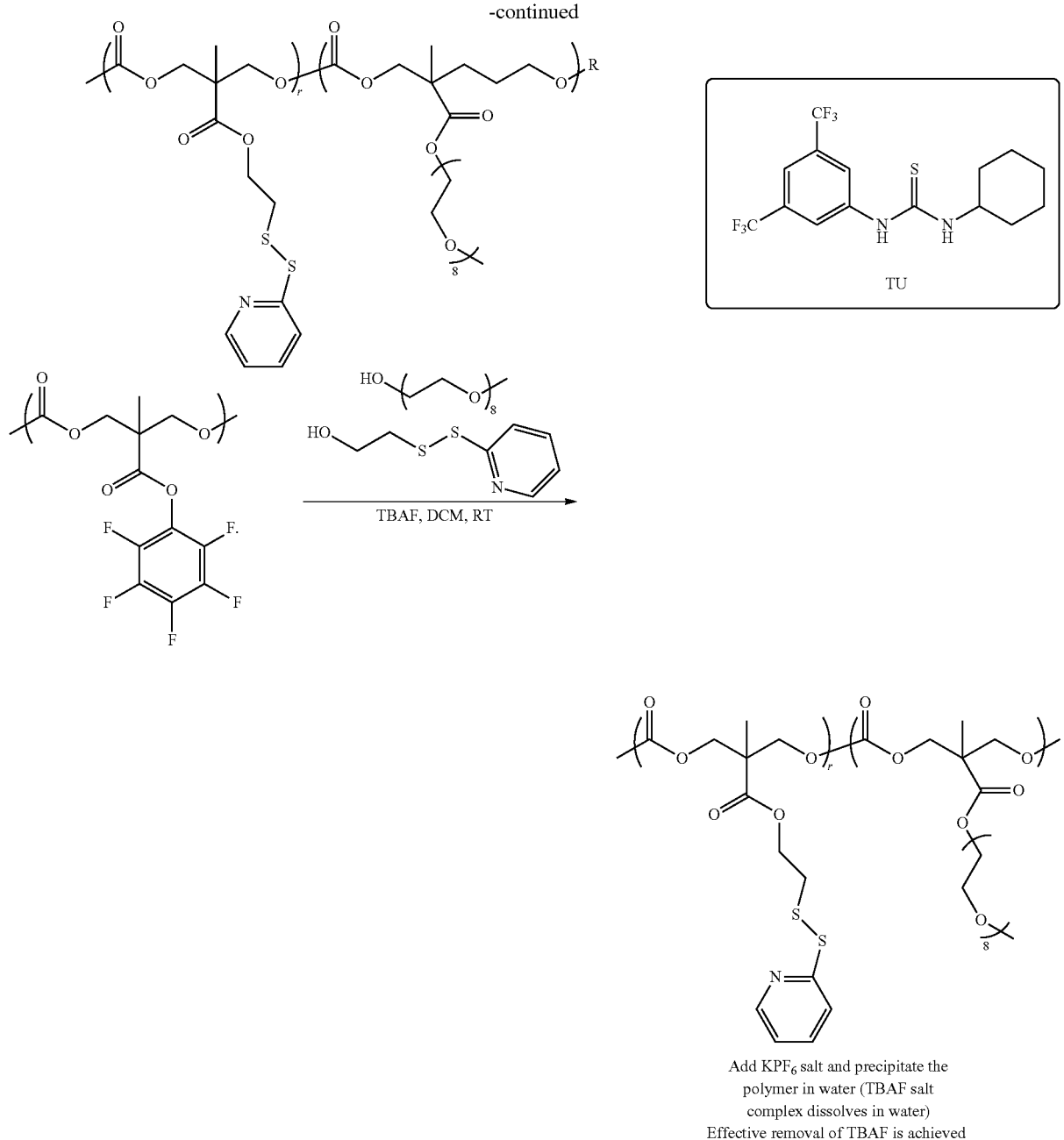

In certain embodiments, the polymer network is formed from a homopolymer via a controlled crosslinking. In certain embodiments, the host crosslinked polymer network is formed from a random copolymer via a controlled crosslinking Depending on the nature of the polymer network and crosslinking, the biological or chemical intervention may be any suitable event, such as a change in pH, redox reagent, redox potential, ionic strength, enzymatic activity, protein concentration, light, heat, or mechanical stress, which intervention leads to a breaking and/or forming of a chemical bond. For example, certain copolymer-based nanoparticles can be rapidly formed by ultraviolet or visible irradiation without the need to use any chemical crosslinkers or agents. The encapsulated guest molecules can be released by ultraviolet or visible irradiation or in the presence of a chemical stimulus such as glutathione if disulfide-bond-forming moieties (or sulfhydryl groups) are also incorporated into the copolymer structure.

In certain embodiments, the one or more functional groups are selected from the group consisting of amino, carboxyl, hydroxyl, halide, acyl halide, ester, azide, nitrile, amide, epoxide, aldehyde, furan, alkene and alkyne, acyl, and thioacyl groups. In certain preferred embodiments, the one or more functional groups are selected from amino, hydroxyl, amide, halide, carboxyl, acyl, thioacyl and ether groups.

The nano-assembly may take any suitable dimensions, for example, having a diameter from about 3 nm to about 300 nm (e.g., about 3 nm to about 200 nm, about 3 nm to about 100 nm, about 3 nm to about 50 nm, about 3 nm to about 30 nm, about 10 nm to about 300 nm, about 30 nm to about 300 nm, about 50 nm to about 300 nm, about 100 nm to about 300 nm).

The non-covalently encapsulated guest molecular cargo may be present in any suitable amounts, for example, accounting for from about 1 wt % to about 45 wt % (e.g., about 1 wt % to about 35 wt %, about 1 wt % to about 25 wt %, about 1 wt % to about 20 wt %, about 1 wt % to about 15 wt %, about 1 wt % to about 10 wt %, about 5 wt % to about 45 wt %, about 10 wt % to about 45 wt %, about 15 wt % to about 45 wt %, about 20 wt % to about 45 wt %) of the nano-assembly.

The guest molecular cargo may be any suitable material, for example, selected from therapeutic, diagnostic or imaging agents. For example, the guest molecular cargo is a small molecule, a polypeptide or an oligonucleotide. In certain embodiments, the guest molecular cargo is an antitumor agent. In certain preferred embodiments, the guest molecular cargo is a hydrophobic molecule.

The functionalized surface of the nanogel may display one or more reactive groups at any suitable density, for example, from very sparingly (e.g., about 0.1%) to full coverage (e.g., about 100%). Thus, for example, the functionalized surface of the nanogel may display reactive groups at a density of, e.g., 1, 2, 5, 10, 20, 30, 40, 50, 60, 70, 80, 90, or 100%.

In yet another aspect, the invention generally relates to a method for controlled delivery of an agent to a target biological site. The method includes: (1) providing a nano-assembly of a host crosslinked polymer network non-covalently encapsulating therein a guest molecular cargo, wherein the host crosslinked polymer network is comprised of biodegradable polymeric backbones and is adapted to partial or complete decrosslinking and/or degraded by a biological, physical or chemical intervention resulting in release of the guest molecular cargo from the nano-assembly; (2) delivering the nano-assembly to the target biological site; and (3) causing a biological, physical or chemical intervention resulting in a partial or complete decrosslinking resulting in release of the guest molecular cargo from the nano-assembly.

In certain preferred embodiments, the guest molecular cargo is selected from a therapeutic, diagnostic or imaging agent. For example, the guest molecular cargo is a small molecule, a peptide or an oligonucleotide. In certain embodiments, the guest molecular cargo is an antitumor agent. In certain embodiments, the target biological site comprises a site inside a cell (e.g., a tumor cell). In certain embodiments, the target biological site comprises a specific tissue (e.g., a tumor tissue). In certain embodiments, the target biological site comprises a site extracellular to a tumor cell. In certain embodiments, the nano-assembly is preferably taken up by a tumor tissue in a physiological environment.

In certain embodiments, the nano-assembly and nanogels of the invention comprise polypeptides with side chain functional groups adapted to incorporate side chain functionalities providing for self-assembly and crosslinking & then decrosslinking based on tissue microenvironment. FIGS. 4-7 illustrate certain exemplary embodiments.

To synthesize a crosslinked polymeric nanogel that contains disulfide crosslinks using GRAS components, it was assumed that degradation of the polymeric nanogel under biological conditions will occur through hydrolysis of esters and amides in addition to the reductive cleavage of the disulfide bonds. (Ulery, et al. 2011 *J. Polym. Sci., Part B: Polym. Phys.* 49, 832-864.) Glutamic acid (a naturally occurring amino acid) and putrescine (one of the growth factors for cell division) were chosen as components of a degradable polyamide backbone. The dicarboxylic acid nature of the glutamic acid and the diamino nature of putrescine was used to synthesize the amide-based polymer backbone. The amino moiety in the glutamic acid was then used as the handle to introduce functional groups that cause self-assembly of this polymer into a nanogel, as well as to incorporate surface functional groups, and the crosslinkable functional groups. The polyamide, from glutamic acid and putrescine, was functionalized with the hydrophilic oligoethyleneglycol (OEG) moiety and the hydrophobic pyridyl disulfide (PDS) moiety. Since this functionalization renders the polymer amphiphilic, this is prone to self-assemble, which can then be converted to a crosslinked polymer nanogel using the recently introduced self-crosslinking strategy using the PDS unit as the handle. (Ryu, et al. 2010 *J. Am. Chem. Soc.* 132, 8246-8247.)

Figure 8:
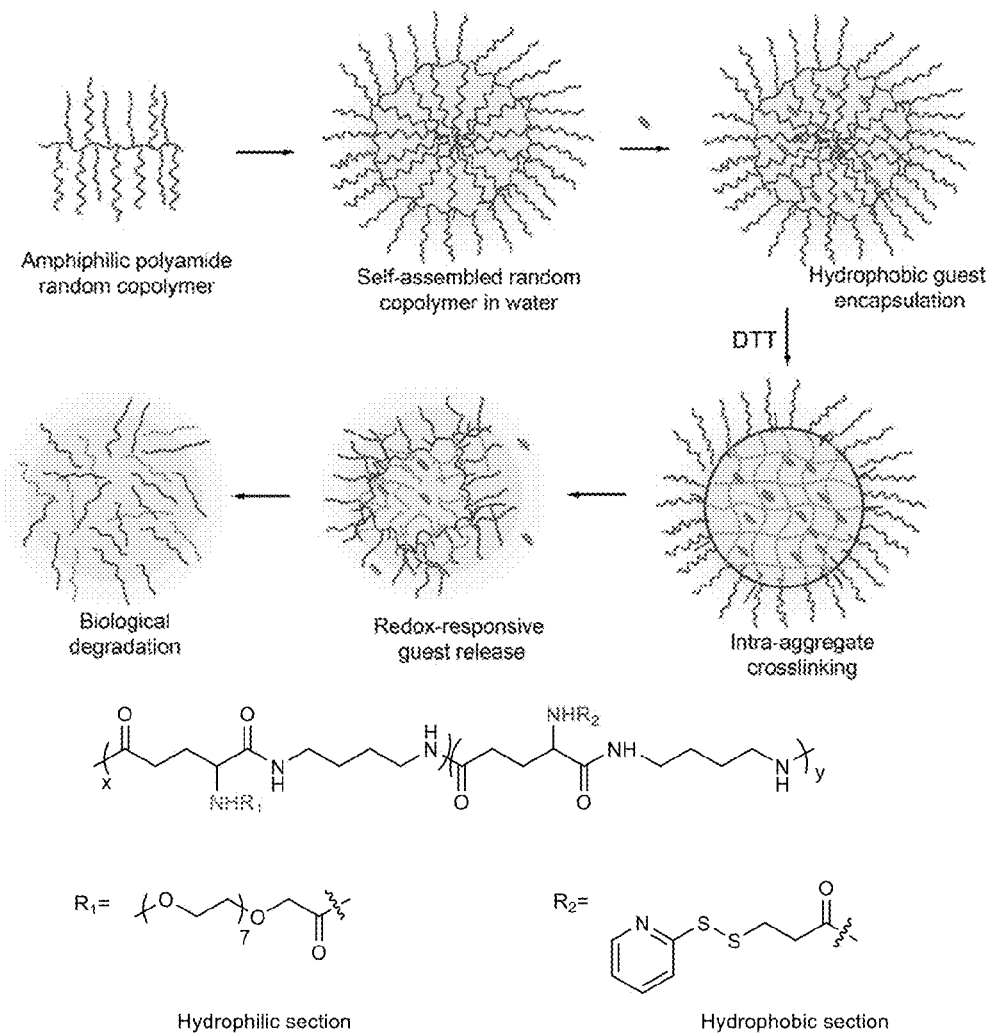
FIG. 8. Scheme 2. Top: Schematic representation of hydrophobic guest encapsulation, followed by redox responsive release and degradation by enzymes; Bottom: Chemical structure of the nanogel precursor polymer.

Similarly, in addition to providing the hydrophilic component, the OEG moiety also has the potential to endow the nanogel with a surface functionality that is known to endow nanocarriers with reduced non-specific interactions in serum. (Peer, et al. 2007 *Nat. Nanotechnol.* 2, 751-760.) Note that the degradation of the side chain functional groups in the nanogel will provide oligoethyleneglycol carboxylic acid and thiopropionic acid, both of which are also considered to be biocompatible and safe. Structures of the targeted polymer and the nanogel are shown in Scheme 2 (FIG. 8).

Figure 9:
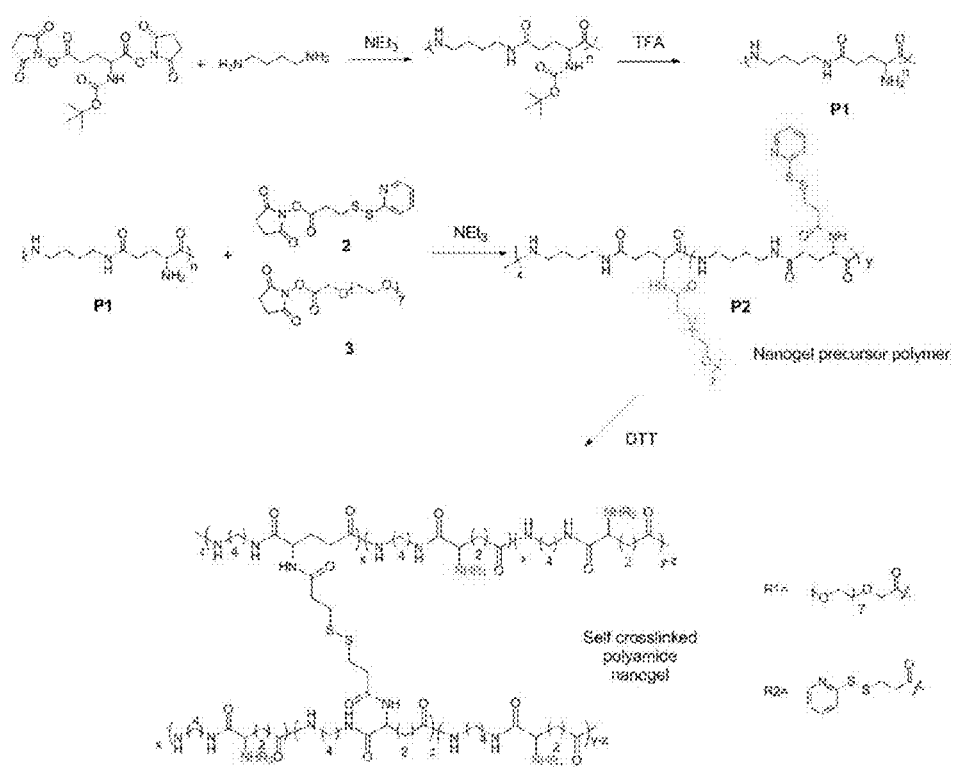
FIG. 9. Scheme 3. Synthetic scheme for the nanogel precursor polymer and nanogel FIG. 10. Self-assembly of polymeric aggregates as seen by a) hydrophobic guest encapsulation b) dynamic light scattering, c) transmission electron microscopy (scale 500 nm)

The precursor polymer was achieved by first synthesizing the polymer backbone with amino moieties of glutamic acid available for post-polymer functionalization. Synthesis of this polymer started with the reaction between the bis-N-hydroxysuccinimide ester of N-Boc-L-glutamic acid (1) and putrescine (2) (Scheme 3, FIG. 9). The resultant copolymer, which was characterized by $^1$H NMR and gel permeation chromatography (GPC), was found to have an $M_n$ of 8.3 kDa (FIG. S1). Removal of the N-boc-moiety from the polymer was achieved using trifluoro acetic acid, the conversion of which was quantitative as discerned by $^1$H NMR. The amine in polymer P1 was then treated with excess but equal amounts of the N-hydroxysuccinimide esters of olgioethyleneglycol monocarboxylic acid and PDS-protected thiopropionic acid, as shown in Scheme 3 (FIG. 9). After removing the excess reagents through dialysis, the final conjugation ratio in the target polymer P2 was determined by $^1$H NMR by the characteristic peaks of the PDS moiety at 8.5 ppm and that of the PEG methoxy group at 3.35 ppm. The ratio of these moieties was found to be 7:3 for the hydrophilic and hydrophobic side chains. The difference in the conjugation ratio is possibly due to the difference in reactivity of the two side chains.

Figure 10:
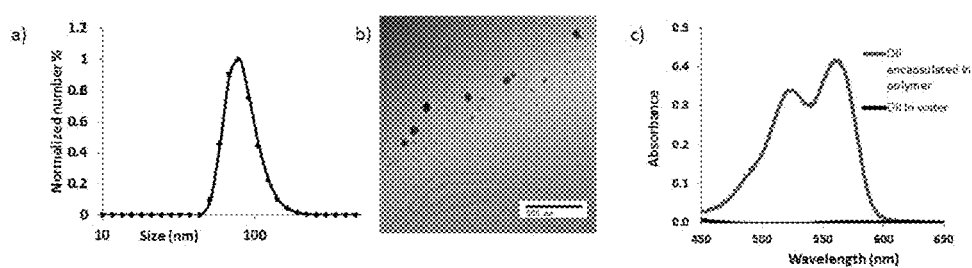

Since the polymer is amphiphilic in nature, it is expected to self-assemble in aqueous solution. This possibility was evaluated using dynamic light scattering (DLS) and hydrophobic dye encapsulation studies in solution, complemented by transmission electron microscopy (TEM) (FIG. 10). DLS experiments were carried out with a 1 mg/mL solution of polymer P2 in water and the aggregates were ~90 nm. Size estimates from TEM also support the DLS measurement. The TEM data also revealed that the assembly has a spherical morphology; the slight departure from a perfectly spherical shape is attributed to the soft nature of the polymer assembly and the nanogel. Although TEM is the dried version of the solution phase assembly, measured in the DLS, since the sizes from these two measurements correlate, it is a reasonable assumption that the morphology of the aggregates is indeed spherical in solution. Next test was whether these amphiphilic polymeric aggregates are capable of encapsulating hydrophobic molecules in an aqueous medium. To test this, a hydrophobic dye 1,1-dioctadecyl-3, 3,3,-tetramethylindocarbocyanine perchlorate (DiI) was used as a fluorescent probe. The dye in itself does not show any absorption in water, as it is not soluble. However, when dissolved in the presence of the polymeric aggregates, its apparent solubility is evident by absorption spectrum (FIG. 10).

Figure 11:
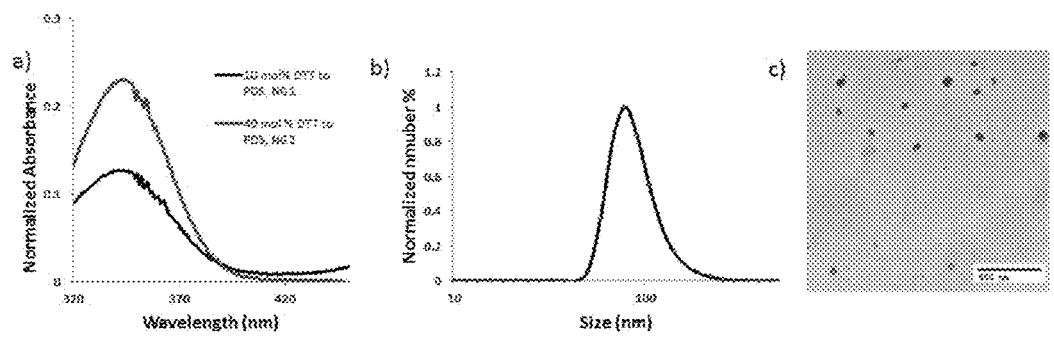
FIG. 11. (a) Absorption spectra of pyridothione in UV-vis. Pyridothione, which is a byproduct during nanogel synthesis by disulfide bond formation and shows characteristic absorption at 343 nm wavelength; b) Size distribution of nanogels in water; c) TEM images of nanogels (scale 500 nm).

To trap the nanoscale aggregates through chemical cross-linking, self-crosslinking strategy was used in which a sub-stoichiometric amount of dithiothreitol (DTT) is added to the solution containing these aggregates. Briefly, DTT executes a rapid cleavage of the disulfide units from the PDS moieties. Since the pyridothione byproduct is stable and unreactive, the thiol moieties generated in the polymer chain now undergo a thiol-disulfide exchange with the remaining PDS units within the aggregate to cause crosslinked polymeric nanogels. A key question here is whether this cross-linking reaction is intra-aggregate or inter-aggregate. If this is intra-aggregate, then the size of the crosslinked nanogel should closely correlate with the amphiphilic aggregate from P2. Indeed, the size of the crosslinked nanogel was found to be very similar to that of the aggregate (FIG. 11). In generating the nanogels, it is also possible to control the crosslink densities by simply varying the amount of DTT added to the reaction mixture. To see whether the extent of crosslinking correlates with the amount of DTT added, the amount of pyridothione generated in the reaction was monitored, which was found to closely correlate with each other. This suggests that the DTT-induced cleavage of the PDS units and the subsequent crosslinking reactions are nearly quantitative. Two nanogels, NG1 and NG2 with 3% and 5% cross-linking densities, respectively, were prepared. NG2 was used for all the subsequent studies outlined below.

Figure 12:
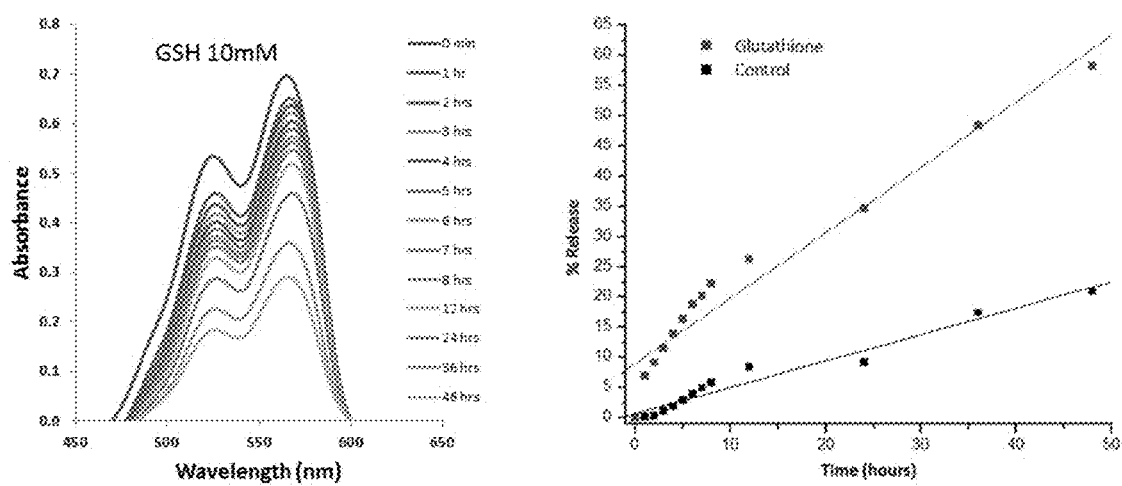
FIG. 12. DiI release from nanogels in response to 10 mM GSH over time.

Once a molecule is encapsulated within the interior, it is also critical to be able to trigger the release of these molecules in response to a specific stimulus. Since the nanogels consist of disulfide crosslinks, they should be responsive to thiol-based reducing environments. Glutathione (GSH) is a reducing agent found in millimolar concentrations in the cytosol, while its concentration in the extracellular environment is micromolar. Thus, the release of the encapsulated dye molecule from the NG2 nanogel scaffold was tested in the presence of 10 mM GSH. It was observed that in the presence of GSH, the guest molecule was released from the nanogel as discerned from the decrease in the absorption spectrum. The decrease in absorbance of DiI is attributed to the precipitation of the rather hydrophobic guest molecule in water, upon release from the nanogel due to the GSH-triggered decrosslinking (FIG. 12). In a control experiment, where no GSH was added to the solution, the decrease in absorbance was much slower which indicates that the guest molecule release is indeed occurring due to the decrosslinking of the nanogel scaffold in the presence of GSH.

Figure 13:
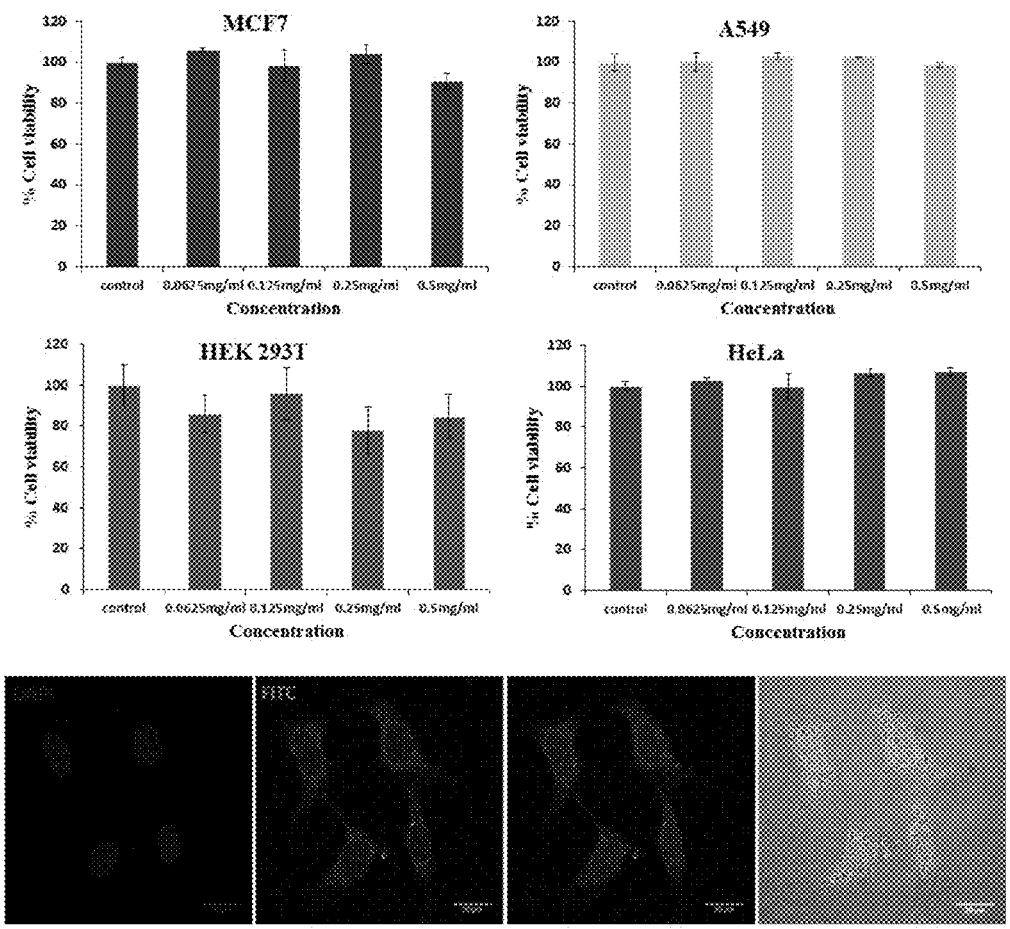
FIG. 13. Top: In vitro cell viability of nanogels on 293T and HeLa cell line after 24 hour of incubation, confocal microscopy images of HeLa cells after incubation for 12 hrs with Middle: DiO loaded nanogels (left: DiO channel, middle: DIC image, right: overlap of both) and Bottom: FITC conjugated nanogels (left to right: DAPI channel, FITC channel, overlap of both channels, DIC image with overlap); Scale (20 µm).

A key motivation behind designing a polymer with GRAS components is to design a polymeric nanogel that exhibits very low toxicity. First tested was the in vitro cellular viability of the nanogels on HEK-293T, MCF7, A549 and HeLa cell lines using the Alamar blue assay. NG2, which was incubated along with cell lines for 24 hours at 37° C., showed high and concentration independent cellular viability for up to a concentration of 0.5 mg/mL (FIG. 13).

Cytotoxicity studies are meaningful, only when the nanoassembly gains access to the cells and still prove not to be cytotoxic. Therefore, it was also tested whether these nanogels can undergo cellular internalization. In vitro cellular uptake of nanogels encapsulated with hydrophobic dye, 3,3'-dioctadecyloxa-carbocyanine perchlorate (DiO) were performed, where the nanogels were incubated with HeLa cells for 12 hours and evaluated by confocal microscopy. It was noted that nanogels enter the cells within this time period and that these are distributed throughout the cytoplasm, as shown in FIG. 13. It is also possible that the guest molecules can leak from the nanogels, where the hydrophobic dyes can passively diffuse into the cells. If DiO escaped the nanogel, it would mainly bind to the cell membrane rather than diffuse into the cytosol.

To confirm that the DiO signal observed was not due to escape from nanogels, fluorescein was covalently attached to the nanogels and examined them for cellular uptake. The fluorescein-labeled nanogels were similarly incubated with HeLa cells for 12 hours at 37° C. and examined by confocal microscopy. It is again clear that the nanogels were not only taken up by the cells, but also are uniformly distributed throughout the cytosol (FIG. 13).

The toxicity of the nanogels was further evaluated using a more rigorous test. Mouse preimplantation embryos were cultured in the presence of nanogels. Preimplantation embryos are generally more sensitive to toxicants than regular somatic cells and must undergo several morphogenetic events in order to successfully develop into a blastocyst over a 4-day period. Perturbations in many cellular events, defective cell cycle and cell lethality are known to disrupt blastocyst development. (Lin, et al. 2009 *Hum. Reprod.* 24, 386-397; Taylor, et al. 2014 *Beilstein J. Nanotechnol.* 5, 677-688; Fleming, et al. 2004 *Biol Reprod.* 71, 1046-1054.) Therefore, assessing the development of embryos in the presence of nanogels is a highly sensitive method for evaluating toxicity.

The development of embryosin culture, with and without nanogels, was carefully monitored. No differences were found in development rate or efficiency of blastocyst formation in the presence of nanogels. Both the control group (KSOM, negative control) and KSOM supplemented with fluorescein-labeled nanogels (nanogel-FITC) developed blastocysts after 4 days in culture (FIG. 13A-B). In addition, fluorescence signal was also detected in nanogel-FITC blastocysts, but not in the negative controls (FIG. 14A-B) indicating that the nanogel-FITC was taken up by blastomeres during preimplantation development, but did not exhibit any disruption to developmental potential of embryos. These results show that the nanogels are highly biocompatible and non-toxic to mammalian preimplantation embryos and pluripotent cells.

Figure 14:
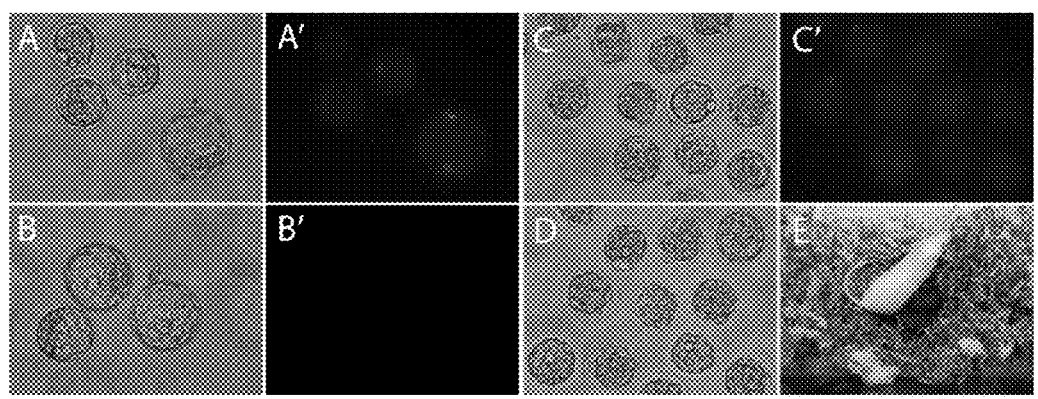
FIG. 14. Mouse blastocyst formation and embryo transfer results. Blastocysts were formed after 4 days of in vitro culture with (A, A') or without (B, B') FITC-nanogels. For in vivo experiment, early embryos were firstly cultured for 3 days in vitro with (C, C') or without (D) FITC-nanogels, then these morulae/early blastocysts were transferred to the uteri of recipients. E, live pups born with nanogel exposure during preimplantation development.

To further investigate toxicity, early blastocysts were transferred into pseudopregnant recipients in order to determine pups can be born after 3 days of preimplantation nanogel exposure. Live pups were born at equivalent rates to controls after preimplantation development in the presence of glutamic acid nanogels (FIG. 14D). Taken together, these results indicate that the glutamic acid nanogels are biocompatible and non-toxic to mammalian preimplantation development, which is quite sensitive to the culture environment and that fetal development after culture in the nanogels is similarly unaffected permitting normal growth and survival to birth. (Watkins, et al. 2008 *Semin. Reprod. Med.* 26, 175-185.)

Thus, a new polyamide has been developed into a nanogel with the building blocks that are based on biocompatible components. The backbone of the polyamide is based on glutamic acid and putrescine, while the side chain substituents are based on oligoethyleneglycol and thiopropionic acid. Since the precursor to these side-chain substituents make the polyamide amphiphilic, the polymer self-assembles in aqueous solutions. Disulfide crosslinked polymeric nanogels have been obtained using this self-assembly, while concurrently taking advantage of the amphiphilic nature of the assembly to sequester hydrophobic molecules within its interior. Since the crosslinks are based on disulfide functionalities, these nanogels exhibit molecular release in response to the intracellular stimulus, glutathione. Finally, to test the versatility of the biocompatible nanogel design, these nanogels were tested for toxicity using a more classical cytotoxicity assay and a more rigorous and highly sensitive mammalian preimplantation development assay. In both assays, the nanogels exhibit no discernible toxicity, suggesting that these GRAS-based stimuli responsive nanogels has great potential for in vivo applications.

EXPERIMENTAL

Materials:

All the reagents were purchased from commercial source and used as such without further purification, unless otherwise mentioned. $^1$H NMR spectra were recorded on a Bruker DPX-400 MHz NMR spectrometer and all the spectra were calibrated against tetramethylsilane (TMS). Dynamic Light Scattering (DLS) measurements were carried out on a Malvern Nanozetasizer. TEM images were recorded on a JEOL-2000FX machine operating at an accelerating voltage of 100 kV cell imaging was performed using a Zeiss 510 META confocal microscope. Fluorescence measurements were performed on a fluorescence plate reader (Molecular Devices, SpectraMax M5).

Synthesis of Polymer 1b:

100 mg (0.226 mmol) of N-boc-L-glutamic acid di-activated ester was added in a round bottom flask with DMF for stirring. 52.47 µL (0.376 mmol) of triethyl amine was then added to the solution followed by adding 22.7 µL (0.226 mmol) of 1, 4 diaminobutane. The reaction was stirred overnight and quenched by cooling it. The final product was purified by precipitating it in diethyl ether followed by dialysis using a cut off membrane of Mn 3.5 kDa in methanol. The product is isolated as an off-white sticky solid. Finally, polymer 1 is obtained by TFA deprotection.

Synthesis of Nanogel Precursor Polymer P2:

75 mg (0.3483 mmol) of polymer 1 and 974 (0.6966 mmol) of triethyl amine was dissolved in DMF in a round bottom flask. 113 mg (0.2786 mmol) of PEG-NHS 3 and 87 mg (0.2786 mmol) of PDS-NHS 2 was then added to the reaction mixture and stirred overnight. The product was then dialyzed in methanol with a 3.5 kDa cutoff membrane.

Procedure for Dye Encapsulation:

The polymer P2 (1 mg/mL) was dissolved in water. 10 µL (0.01 mg) of DiI (1 mg/mL in acetone) was added to the stirring solution of polymer followed by the desired amount of DTT for crosslinking. The mixture was stirred overnight at room temperature, open to the atmosphere allowing the organic solvent to evaporate. Excess insoluble DiI was removed by filtration and pyridothione was removed from the nanogel solution by dialysis using a membrane with molecular cut-off of 3.5 kDa Dynamic Light Scattering (DLS) Study:

For the DLS measurements, the concentration of the polymer and nanogel solution was 1 mg/mL. The solution was filtered using a hydrophilic membrane (pore size 0.450 µm) before experiment was performed.

Transmission Electron Microscope (TEM) Study:

For the TEM measurements the nanogel solution was prepared in 1 mg/mL concentration. One drop of the sample was dropcasted on carbon coated Cu grid. About 3 min after the deposition, the grid was tapped with filter paper to remove surface water. Finally, it was dried in air for another 6 h before images were taken.

In Vitro Cell Viability:

The in vitro cellular viability of the nanogels was evaluated on healthy HEK293T, MCF7, A549, and HeLa cancer cell lines. The cells were cultured in T75 cell culture flasks using Dulbecco's Modified Eagle Medium/Nutrient Mixture F-12 (DMEM/F12) with 10% fetal bovine serum (FBS) supplement. The cells were seeded at 10,000 cells/well/200 µL in a 96 well plate and allowed to grow for 24 hours under incubation at 37° C. and 5% $CO_2$. These cells were then treated with nanogels of different concentrations and were incubated for another 24 hours. Cell viability was measured using the Alamar Blue assay with each data point measured in triplicate. Fluorescence measurements were made using the plate reader SpectraMax M5 by setting the excitation wavelength at 560 nm and monitoring emission at 590 nm on a black well plate.

In Vitro Cell Uptake:

FITC labeled nanogels was synthesized using the amines in the polymer for conjugation with FITC. In a vial, polymer was dissolved in methanol and excess FITC was added. The solution was let to stir overnight followed by extensive dialysis in methanol using cut off membrane $M_n$-3500 Da. Nanogel was prepared using the same procedure as described previously.

In a glass bottom dish, HeLa cells were incubated overnight at 37° C. and 5% $CO_2$ with nutrient medium (DMEM/F12 with 10% fetal bovine serum supplement). The nutrient medium was then taken out and the cells were washed with pH 7.4 PBS buffer. To it 100 µL of the nanogel solution (10 mg/mL) either encapsulated with DiO or conjugated with FITC were added along with the nutrient medium. The cells were then incubated for 30 min at 37° C. and the fluorescence was observed under a confocal microscope (63× oil immersion objective)

Embryo Recovery and Culture:

B6D2F1 female mice (8 to 10 weeks old) were induced to superovulate with 5 IU pregnant mare's serum gonadotropin (PMSG, Sigma), followed 46-48 h later by 5 IU human chorionic gonadotropin (hCG, Sigma). Females were mated with B6D2F1 males immediately after hCG injection, and euthanized at 20-22 h post-hCG injection. Oviductal ampullae were cut open to release zygotes, and cumulus cells were removed by pipetting in M2 medium (Millipore) containing 0.1% hyaluronidase (Sigma). Zygotes were cultured in KSOM medium (Millipore) or KSOM supplemented with 1 mg/mL of nanogel solution at 37° C., 5% $CO_2$/5% $O_2$ balanced in $N_2$ for 4 days. Use of vertebrate animals for embryo production was approved by the University of Massachusetts IACUC.

Embryo Transfer:

Morulae/early blastocysts after 3 days of culture in KSOM or KSOM supplemented with nanogels were transferred into uteri of 2.5 dpc (day post coitus) pseudopregnant foster dams (CD-1 mice, albino) by using the non-surgical embryo transfer (NSET) device. Recipient females were allowed to deliver pups naturally in order to observe production of live healthy animals after preimplantation development in the presence of nanogel solution.

In this specification and the appended claims, the singular forms "a," "an," and "the" include plural reference, unless the context clearly dictates otherwise. Unless defined otherwise, all technical and scientific terms used herein have the same meaning as commonly understood too one of ordinary skill in the art. Unless defined otherwise, all technical and scientific terms used herein have the same meaning as commonly understood by one of ordinary skill in the art. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A crosslinked biodegradable polymer comprising a polymeric backbone biodegradable into small molecules in response to a relevant biological, physical or chemical stimuli, wherein the polymer comprises the structure of:

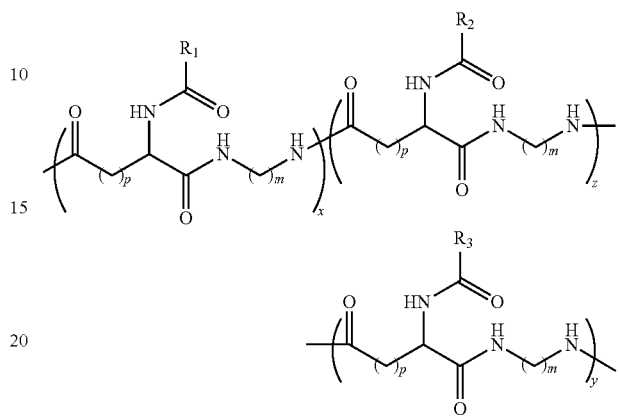

wherein
each p is independently an integer from about 1 to about 6,
each m is independently an integer from about 1 to about 6,
each of x and y is independently a positive number, z is zero or a positive number,
$R_1$ is a charge-neutral hydrophilic group,
$R_2$ comprises a crosslinking moiety, and
$R_3$ comprises a non-crosslinking group.

2. The crosslinked biodegradable polymer of claim 1, wherein the polymeric backbone is biodegradable into molecules that are generally regarded as safe (GRAS).

3. A crosslinked polyamide nanogel, wherein the nanogel comprises the structure of:

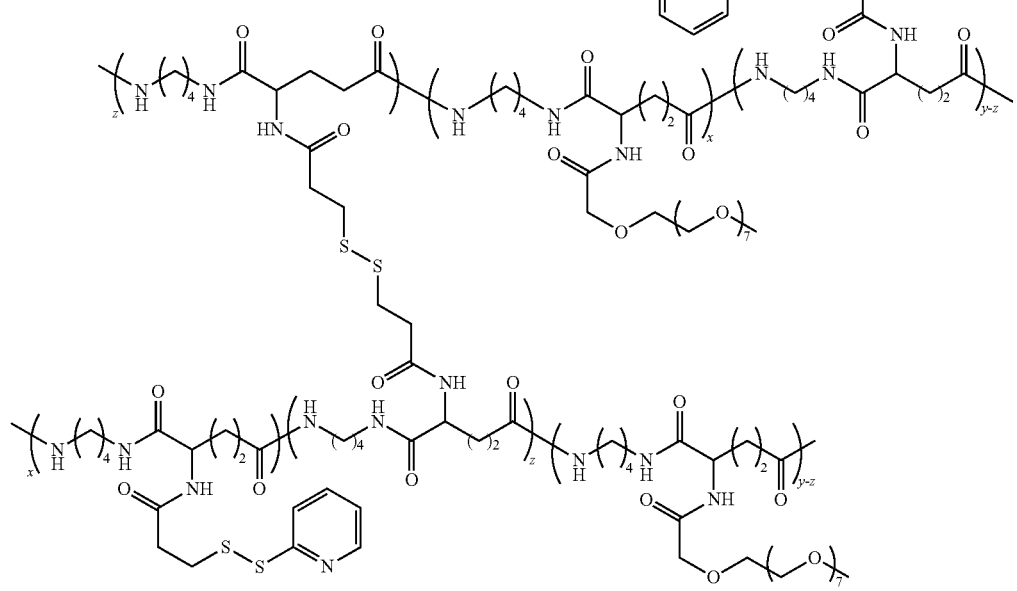

each of x, y and z is independently a positive number.

4. A polymeric nanogel comprising the crosslinked biodegradable polymer of claim 1.

* * * * *